(12) United States Patent
Gaudreau et al.

(10) Patent No.: US 10,533,036 B2
(45) Date of Patent: Jan. 14, 2020

(54) CLOSTRIDIUM DIFFICILE TOXINS A AND/OR B ANTIGEN AND EPITOPE ANTIBODY, AND PHARMACEUTICAL USES THEREOF

(71) Applicant: Immune Biosolutions Inc., Sherbrooke (CA)

(72) Inventors: Simon Gaudreau, Sherbrooke (CA); Martin Cloutier, Sherbrooke (CA); Louis-Charles Fortier, Sherbrooke (CA); Frederic Leduc, Sherbrooke (CA); Maxime Tremblay, Sherbrooke (CA); Steeve Veronneau, Cookshire-Eaton (CA); Djorjde Gbric, Sherbrooke (CA); Jean-Francois Larrivee, Sherbrooke (CA)

(73) Assignee: IMMUNE BIOSOLUTIONS INC, Sherbrooke (CA)

( * ) Notice: Subject to any disclaimer, the term of this patent is extended or adjusted under 35 U.S.C. 154(b) by 0 days.

(21) Appl. No.: 15/551,848

(22) PCT Filed: Feb. 19, 2016

(86) PCT No.: PCT/CA2016/050170
§ 371 (c)(1),
(2) Date: Aug. 17, 2017

(87) PCT Pub. No.: WO2016/131157
PCT Pub. Date: Aug. 25, 2016

(65) Prior Publication Data
US 2018/0022784 A1    Jan. 25, 2018

Related U.S. Application Data
(60) Provisional application No. 62/118,450, filed on Feb. 19, 2015.

(51) Int. Cl.
| | |
|---|---|
| *C07K 14/33* | (2006.01) |
| *C07K 16/12* | (2006.01) |
| *C07K 16/46* | (2006.01) |
| *C12N 15/85* | (2006.01) |
| *A61K 39/08* | (2006.01) |
| *A61K 39/00* | (2006.01) |

(52) U.S. Cl.
CPC .......... *C07K 14/33* (2013.01); *C07K 16/1282* (2013.01); *C07K 16/46* (2013.01); *C12N 15/85* (2013.01); *A61K 39/08* (2013.01); *A61K 2039/505* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 7,625,559 | B2 * | 12/2009 | Ambrosino | A61K 39/08 424/139.1 |
| 2014/0271700 | A1 * | 9/2014 | Chong | C07K 14/33 424/190.1 |

FOREIGN PATENT DOCUMENTS

| | | | |
|---|---|---|---|
| WO | 2012/028741 A1 | 3/2012 | |
| WO | WO-2012028741 A1 * | 3/2012 | ............ A61K 39/08 |
| WO | 2014045226 A1 | 3/2014 | |
| WO | 2014060898 A1 | 4/2014 | |
| WO | 2016/131157 | 8/2016 | |

OTHER PUBLICATIONS

Permpoonpattana et al. Infection and Immunity, vol. 79, No. 6, Jun. 2011, p. 2295-2302.*
Hassoun, A. and F. Ibrahim (2007). "Use of intravenous immuno-globulin for the treatment of severe Clostridium difficile colitis." Am J Geriatr Pharmacother 5(1): 48-51.
Johal, S. S., C. P. Lambert, et al. (2004). "Colonic IgA producing cells and macrophages are reduced in recurrent and non-recurrent Clostridium difficile associated diarrhoea." J Clin Pathol 57(9): 973-9.
Johnson, S. (2009). "Recurrent Clostridium difficile infection: a review of risk factors, treatments, and outcomes." J Infect 58(6): 403-10.
Kelly, C. P., C. Pothoulakis, et al. (1994). "Clostridium difficile colitis." N Engl J Med 330(4): 257-62.
Kyne, L., M. B. Hamel, et al. (2002). "Health care costs and mortality associated with nosocomial diarrhea due to Clostridium difficile." Clin Infect Dis 34(3): 346-53.
Kyne, L., M. Warny, et al. (2001). "Association between antibody response to toxin A and protection against recurrent Clostridium difficile diarrhoea." Lancet 357(9251): 189-93.
Leung, D. Y., C. P. Kelly, et al. (1991). "Treatment with intravenously administered gamma globulin of chronic relapsing colitis induced by Clostridium difficile toxin." J Pediatr 118(4 Pt 1): 633-7.

(Continued)

*Primary Examiner* — Oluwatosin A Ogunbiyi
(74) *Attorney, Agent, or Firm* — Lavery, De Billy, LLP; Alain Dumont

(57) ABSTRACT

It is described a *Clostridium difficile* (*C-difficile*) toxins A and/or B as a target for therapy, including passive immunotherapy, and particularly prevention of *C-difficile* intoxication in human or other animals. It is also described a polypeptide comprising a portion of *C-difficile* toxins A and/or B sequence being an epitope for anti-toxins A and/or B antibody. It is also disclosed a method for generating a neutralizing antibody directed against *C-difficile* toxins A and/or B. It is also provided a novel formulation that combines key toxins A and/or B epitope antibodies, located in three key domains of toxins A and/or B, for neutralizing toxins A and/or B, at any stage of toxins A and/or B intoxication related to *C-difficile* infection. The novel formulation of toxins A and/or B epitope antibodies are useful in immunotherapy, for therapeutic and/or prophylactic mediation of *C-difficile* intoxication.

17 Claims, 10 Drawing Sheets
Specification includes a Sequence Listing.

(56) References Cited

OTHER PUBLICATIONS

Lyerly, D. M., E. F. Bostwick, et al. (1991). "Passive immunization of hamsters against disease caused by Clostridium difficile by use of bovine immunoglobulin G concentrate." Infect Immun 59(6): 2215-8.

McPherson, S., C. J. Rees, et al. (2006). "Intravenous immunoglobulin for the treatment of severe, refractory, and recurrent Clostridium difficile diarrhea." Dis Colon Rectum 49(5): 640-5.

O'Connor, J. R., S. Johnson, et al. (2009). "Clostridium difficile infection caused by the epidemic Bi/NAP1/027 strain." Gastroenterology 136(6): 1913-24.

Pepin, J., N. Saheb, et al. (2005). "Emergence of fluoroquinolones as the predominant risk factor for Clostridium difficile-associated diarrhea: a cohort study during an epidemic in Quebec." Clin Infect Dis 41(9): 1254-60.

Salcedo, J., S. Keates, et al. (1997). "Intravenous immunoglobulin therapy for severe Clostridium difficile colitis." Gut 41(3): 366-70.

Songer, J. G. (2004). "The emergence of Clostridium difficile as a pathogen of food animals." Anim Health Res Rev 5 (2): 321-6.

Tjellstrom, B., L. Stenhammar, et al. (1993). "Oral immunoglobulin a supplement in treatment of Clostridium difficile enteritis." Lancet 341(8846): 701-2.

Viscidi, R., B. E. Laughon, et al. (1983). "Serum antibody response to toxins A and B of Clostridium difficile." J Infect Dis 148(1): 93-100.

Warny, M., A. Fatimi, et al. (1999). "Bovine immunoglobulin concentrate-clostridium difficile retains C difficile toxin neutralising activity after passage through the human stomach and small intestine." Gut 44(2): 212-7.

Warny, M., J. Pepin, et al. (2005). "Toxin production by an emerging strain of Clostridium difficile associated with outbreaks of severe disease in North America and Europe." Lancet 366(9491): 1079-84.

Written opinion of the International Searching Authority of PCT/CA2016/050170.

Lyerly, D. M., et al., "Passive immunization of hamsters against disease caused by Clostridium difficile by use of bovine immunoglobulin G concentrate", Infection and Immunity, Jun. 1991 (Jun. 1991) vol. 59, pp. 2215-2218.

Babcock, G. J., T. J. Broering, et al. (2006). "Human monoclonal antibodies directed against toxins A and B prevent Clostridium difficile-induced mortality in hamsters." Infect Immun 74(11): 6339-47.

Corthier, G., M. C. Muller, et al. (1991). "Protection against experimental pseudomembranous colitis in gnotobiotic mice by use of monoclonal antibodies against Clostridium difficile toxin A." Infect Immun 59(3): 1192-5.

Gardiner, D. F., T. Rosenberg, et al. (2009). "A DNA vaccine targeting the receptor-binding domain of Clostridium difficile toxin A." Vaccine 27(27): 3598-604.

Giannasca, P. J., Z. X. Zhang, et al. (1999). "Serum antitoxin antibodies mediate systemic and mucosal protection from Clostridium difficile disease in hamsters." Infect Immun 67(2): 527-38.

Jank, T. and K. Aktories (2008). "Structure and mode of action of clostridial glucosylating toxins: the ABCD model." Trends Microbiol 16(5): 222-9.

Jank, T., T. Giesemann, et al. (2007). "Rho-glucosylating Clostridium difficile toxins A and B: new insights into structure and function." Glycobiology 17(4): 15R-22R.

Johal, S. S., C. P. Lambert, et al. (2004). "Colonic IgA producing cells and macrophages are reduced in recurrent and non-recurrent Clostridium difficile associated diarrhoea." J Clin Pathol 57: 973-9.

Juang, P., S. J. Skledar, et al. (2007). "Clinical outcomes of intravenous immune globulin in severe clostridium difficile-associated diarrhea." Am J Infect Control 35(2): 131-7.

Katchar, K., C. P. Taylor, et al. (2007). "Association between IgG2 and IgG3 subclass responses to toxin A and recurrent Clostridium difficile-associated disease." Clin Gastroenterol Hepatol 5(6): 707-13.

Kelly, C. P., C. Pothoulakis, et al. (1992). "Human colonic aspirates containing immunoglobulin A antibody to Clostridium difficile toxin A inhibit toxin A-receptor binding." Gastroenterology 102(1): 35-40.

Kelly, C. P., C. Pothoulakis, et al. (1996). "Anti-Clostridium difficile bovine immunoglobulin concentrate inhibits cytotoxicity and enterotoxicity of C. difficile toxins." Antimicrob Agents Chemother 40(2): 373-9.

Kink, J. A. and J. A. Williams (1998). "Antibodies to recombinant Clostridium difficile toxins A and B are an effective treatment and prevent relapse of C. difficile-associated disease in a hamster model of infection." Infect Immun 66(5): 2018-25.

Kyne, L., M. B. Hamel, et al. (2002). "Health care costs and mortality associated with nosocomial diarrhea due to Clostridium difficile." Clin Infect Dis 34: 346-53.

Kyne, L., M. Warny, et al. (2000). "Asymptomatic carriage of Clostridium difficile and serum levels of IgG antibody against toxin A." N Engl J Med 342(6): 390-7.

Leffler, D. A. and J. T. Lamont (2009). "Treatment of Clostridium difficile-associated disease." Gastroenterology 136(6): 1899-912.

Lowy, I., D. C. Molrine, et al. "Treatment with monoclonal antibodies against Clostridium difficile toxins." N Engl J Med 362(3): 197-205.

Lyras, D., J. R. O'Connor, et al. (2009). "Toxin B is essential for virulence of Clostridium difficile." Nature 458(7242): 1176-9.

O'Connor et al.: (2009) "Clostridium difficile infection caused by the epidemic BI/NAP1/027 strain"; Gastroenterology 136(6): 1913-24.

Pepin, J., N. Saheb, et al. (2005). "Emergence of fluoroquinolones as the predominant risk factor for Clostridium difficile-associated diarrhea: a cohort study during an epidemic in Quebec." Clin Infect Dis 41: 1254-60.

Rupnik, M., M. H. Wilcox, et al. (2009). "Clostridium difficile infection: new developments in epidemiology and pathogenesis." Nat Rev Microbiol 7(7): 526-36.

Salcedo, J., S. Keates, et al. (1997). "Intravenous immunoglobulin therapy for severe Clostridium difficile colitis." Gut 41: 366-70.

Warny, M., A. Fatimi, et al. (1999). "Bovine immunoglobulin concentrate-clostridium difficile retains C difficile toxin neutralising activity after passage through the human stomach and small intestine." Gut 44: 212-7.

Warny, M., J. Pepin, et al. (2005). "Toxin production by an emerging strain of Clostridium difficile associated with outbreaks of severe disease in North America and Europe." Lancet 366: 1079-84.

Warny, M., J. P. Vaerman, et al. (1994). "Human antibody response to Clostridium difficile toxin A in relation to clinical course of infection." Infect Immun 62(2): 384-9.

Wilcox, M. H. (2004). "Descriptive study of intravenous immunoglobulin for the treatment of recurrent Clostridium difficile diarrhoea." J Antimicrob Chemother 53(5): 882-4.

Wilkins, T. D. and D. M. Lyerly (2003). "Clostridium difficile testing: after 20 years, still challenging." J Clin Microbiol 41 (2): 531-4.

International Search Report of PCT/CA2016/050170.

Examination Report dated May 15, 2019 in respect of corresponding EP application No. 16 751 875.2.

* cited by examiner

MSLISKEELIKLAYSIRPRENEYKTILTNLDEYNKLTTNNNENKYLQLKKILNESIDVFMN
KYKTSSRNRALSNLKKDILKEVILIKNSNTSPVEKNLHFVWIGGEVSDIALEYIKQWADI
NAEYNIKLWYDSEAFLVNTLKKAIVESSTTEALQLLEEEIQNPQFDNMKFYKKRMEFIYD
RQKRFINYYKSQINKPTVPTIDDIIKSHLVSEYNRDETVLESYRTNSLRKINSNHGIDIR
ANSLFTEQELLNIYSQELLNRGNLAAASDIVRLLALKNFGGVYLDVDMLPGIHSDLFKTI — 40
SRPSSIGLDRWEMIKLEAIMKYKKYINNYTSENFDKLDQQLKDNFKLIIESKSEKSEIFS
KLENLNVSDLEIKIAFALGSVINQALISKQGSYLTNLVIEQVKNRYQFLNQHLNPAIESD
NNFTDTTKIFHDSLFNSATAENSMFLTKIAPYLQVGFMPEARSTISLSGPGAYASAYYDF
INLQENTIEKTLKASDLIEFKFPENNLSQLTEQEINSLWSFDQASAKYQFEKYVRDYTGG
SLSEDNGVDFNKNTALDKNYLLNNKIPSNNVEEAGSKNYVHYIIQLQGDDISYEATCNLF
SKNPKNSIIIQRNMNESAKSYFLSDDGESILELNKYRIPERLKNKEKVKVTFIGHGKDEF
NTSEFARLSVDSLSNEISSFLDTIKLDISPKNVEVNLLGCNMFSYDFNVEETYPGKLLLS — 30
IMDKITSTLPDVNKNSITIGANQYEVRINSEGRKELLAHSGKWINKEEAIMSDLSSKEYI
FFDSIDNKLKAKSKNIPGLASISEDIKTLLLDASVSPDTKFILNNLKLNIESSIGDYIYY
EKLEPVKNIIHNSIDDLIDEFNLLENVSDELYELKKLNNLDEKYLISFEDISKNNSTYSV
RFINKSNGESVYVETEKEIFSKYSEHITKEISTIKNSIITDVNGNLLDNIQLDHTSQVNT
LNAAFFIQSLIDYSSNKDVLNDLSTSVKVQLYAQLFSTGLNTIYDSIQLVNLISNAVNDT
INVLPTITEGIPIVSTILDGINLGAAIKELLDEHDPLLKKELEAKVGVLAINMSLSIAAT
VASIVGIGAEVTIFLLPIAGISAGIPSLVNNELILHDKATSVVNYFNHLSESKKYGPLKT
EDDKILVPIDDLVISEIDFNNNSIKLGTCNILAMEGGSGHTVTGNIDHFFSSPSISSHIP
SLSIYSAIGIETENLDFSKKIMMLPNAPSRVFWWETGAVPGLRSLENDGTRLLDSIRDLY
PGKFYWRFYAFFDYAITTLKPVYEDTNIKIKLDKDTRNFIMPTITTNEIRNKLSYSFDGA — 20
GGTYSLLLSSYPISTNINLSKDDLWIFNIDNEVREISIENGTIKKGKLIKDVLSKIDINK
NKLIIGNQTIDFSGDIDNKDRYIFLTCELDDKISLIIEINLVAKSYSLLLSGDKNYLISN
LSNTIEKINTLGLDSKNIAYNYTDESNNKYFGAISKTSQKSIIHYKKDSKNILEFYNDST
LEFNSKDFIAEDINVFMKDDINTITGKYYVDNNTDKSIDFSISLVSKNQVKVNGLYLNES
VYSSYLDFVKNSDGHHNTSNFMNLFLDNISFWKLGFENINFVIDKYFTLVGKTNLGYVE
FICDNNKNIDIYFGEWKTSSSKSTIFSGNGRNVVVEPIYNPDTGEDISTSLDFSYEPLYG
IDRYINKVLIAPDLYTSLININTNYYSNEYYPEIIVLNPNTFHKKVNINLDSSSFEYKWS
TEGSDFILVRYLEESNKKILQKIRIKGILSNTQSFNKMSIDFKDIKKLSLGYIMSNFKSF
NSENELDRDHLGFKIIDNKTYYYDEDSKLVKGLININNSLFYFDPIEFNLVTGWQTINGK
KYYFDINTGAALTSYKIINGKHFYFNNDGVMQLGVFKGPDGFEYFAPANTQNNNIEGQAI
VYQSKFLTLNGKKYYFDNNSKAVTGWRIINNEKYYFNPNNAIAAVGLQVIDNNKYYFNPD
TAIISKGWQTVNGSRYYFDTDTAIAFNGYKTIDGKHFYFDSDCVVKIGVFSTSNGFEYFA
PANTYNNNIEGQAIVYQSKFLTLNGKKYYFDNNSKAVTGLQTIDSKKYYFNTNTAEAATG
WQTIDGKKYYFNTNTAEAATGWQTIDGKKYYFNTNTAIASTGYTIINGKHFYFNTDGIMQ
IGVFKGPNGFEYFAPANTDANNIEGQAILYQNEFLTLNGKKYYFGSDSKAVTGWRIINNK
KYYFNPNNAIAAIHLCTINNDKYYFSYDGILQNGYITIERNNFYFDANNESKMVTGVFKG
PNGFEYFAPANTHNNNIEGQAIVYQNKFLTLNGKKYYFDNDSKAVTGWQTIDGKKYYFNL — 10
NTAEAATGWQTIDGKKYYFNLNTAEAATGWQTIDGKKYYFNTNTFIASTGYTSINGKHFY
FNTDGIMQIGVFKGPNGFEYFAPANTDANNIEGQAILYQNKFLTLNGKKYYFGSDSKAVT
GLRTIDGKKYYFNTNTAVAVTGWQTINGKKYYFNTNTSIASTGYTIISGKHFYFNTDGIM
QIGVFKGPDGFEYFAPANTDANNIEGQAIRYQNRFLYLHDNIYYFGNNSKAATGWVTIDG
NRYYFEPNTAMGANGYKTIDNKNFYFRNGLPQIGVFKGSNGFEYFAPANTDANNIEGQAI
RYQNRFLHLLGKIYYFGNNSKAVTGWQTINGKVYYFMPDTAMAAAGGLFEIDGVIYFFGV
DGVKAPGIYG

FIGURE 2A

MSLVNRKQLEKMANVRFRTQEDEYVAILDALEEYHNMSENTVVEKYLKLKDINSLTDIYI
DTYKKSGRNKALKKFKEYLVTEVLELKNNNLTPVEKNLHFVWIGGQINDTAINYINQWKD
VNSDYNVNVFYDSNAFLINTLKKTVVESAINDTLESFRENLNDPRFDYNKFFRKRMEIIY
DKQKNFINYYKAQREENPELIIDDIVKTYLSNEYSKEIDELNTYIEESLNKITQNSGNDV
RNFEEFKNGESFNLYEQELVERWNLAAASDILRISALKEIGGMYLDVDMLPGIQPDLFES ⎤
IEKPSSVTVDFWEMTKLEAIMKYKEYIPEYTSEHFDMLDEEVQSSFESVLASKSDKSEIF  ⎟— 40
SSLGDMEASPLEVKIAFNSKGIINQGLISVKDSYCSNLIVKQIENRYKILNNSLNPAISE
DNDFNTTTNTFIDSIMAEANADNGRFMMELGKYLRVGFFPDVKTTINLSGPEAYAAAYQD
LLMFKEGSMNIHLIEADLRNFEISKTNISQSTEQEMASLWSFDDARAKAQFEEYKRNYFE ⎦
GSLGEDDNLDFSQNIVVDKEYLLEKISSLARSSERGYIHYIVQLQGDKISYEAACNLFAK ⎤
TPYDSVLFQKNIEDSEIAYYYNPGDGEIQEIDKYKIPSIISDRPKIKLTFIGHGKDEFNT  ⎟— 30
DIFAGFDVDSLSTEIEAAIDLAKEDISPKSIEINLLGCNMFSYSINVEETYPGKLLLKVK
DKISELMPSISQDSIIVSANQYEVRINSEGRRELLDHSGEWINKEESIIKDISSKEYISF ⎦
NPKENKITVKSKNLPELSTLLQEIRNNSNSSDIELEEKVMLTECEINVISNIDTQIVEER ⎤
IEEAKNLTSDSINYIKDEFKLIESISDALCDLKQQNELEDSHFISFEDISETDEGFSIRF
INKETGESIFVETEKTIFSEYANHITEEISKIKGTIFDTVNGKLVKKVNLDTTHEVNTLN
AAFFIQSLIEYNSSKESLSNLSVAMKVQVYAQLFSTGLNTITDAAKVVELVSTALDETID
LLPTLSEGLPIIATIIDGVSLGAAIKELSETSDPLLRQEIEAKIGIMAVNLTTATTAIIT
SSLGIASGFSILLVPLAGISAGIPSLVNNELVLRDKATKVVDYFKHVSLVETEGVFTLLD
DKIMMPQDDLVISEIDFNNNSIVLGKCEIWRMEGGSGHTVTDDIDHFFSAPSITYREPHL
SIYDVLEVQKEELDLSKDLMVLPNAPNRVFAWETGWTPGLRSLENDGTKLLDRIRDNYEG
EFYWRYFAFIADALITTLKPRYEDTNIRINLDSNTRSFIVPIITTEYIREKLSYSFYGSG  ⎟— 20
GTYALSLSQYNMGINIELSESDVWIIDVDNVVRDVTIESDKIKKGDLIEGILSTLSIEEN
KIILNSHEINFSGEVNGSNGFVSLTFSILEGINAIIEVDLLSKSYKLLISGELKILMLNS
NHIQQKIDYIGFNSELQKNIPYSFVDSEGKENGFINGSTKEGLFVSELPDVVLISKVYMD
DSKPSFGYYSNNLKDVKVITKDNVNILTGYYLKDDIKISLSLTLQDEKTIKLNSVHLDES
GVAEILKFMNRKGNTNTSDSLMSFLESMNIKSIFVNFLQSNIKFILDANFIISGTTSIGQ
FEFICDENDNIQPYFIKFNTLETNYTLYVGNRQNMIVEPNYDLDDSGDISSTVINFSQKY
LYGIDSCVNKVVISPNIYTDEINITPVYETNNTYPEVIVLDANYINEKINVNINDLSIRY
VWSNDGNDFILMSTSEENKVSQVKIRFVNVFKDKTLANKLSFNFSDKQDVPVSEIILSFT ⎦
PSYYEDGLIGYDLGLVSLYNEKFYINNFGMMVSGLIYINDSLYYFKPPVNNLITGFVTVG ⎤
DDKYYFNPINGGAASIGETIIDDKNYYFNQSGVLQTGVFSTEDGFKYFAPANTLDENLEG
EAIDFTGKLIIDENIYYFDDNYRGAVEWKELDGEMHYFSPETGKAFKGLNQIGDYKYYFN
SDGVMQKGFVSINDNKHYFDDSGVMKVGYTEIDGKHFYFAENGEMQIGVFNTEDGFKYFA
HHNEDLGNEEGEEISYSGILNFNNKIYYFDDSFTAVVGWKDLEDGSKYYFDEDTAEAYIG  ⎟— 10
LSLINDGQYYFNDDGIMQVGFVTINDKVFYFSDSGIIESGVQNIDDNYFYIDDNGIVQIG
VFDTSDGYKYFAPANTVNDNIYGQAVEYSGLVRVGEDVYYFGETYTIETGWIYDMENESD
KYYFNPETKKACKGINLIDDIKYYFDEKGIMRTGLISFENNNYYFNENGEMQFGYINIED
KMFYFGEDGVMQIGVFNTPDGFKYFAHQNTLDENFEGESINYTGWLDLDEKRYYFTDEYI ⎦
AATGSVIIDGEEYYFDPDTAQLVISE

FIGURE 2B

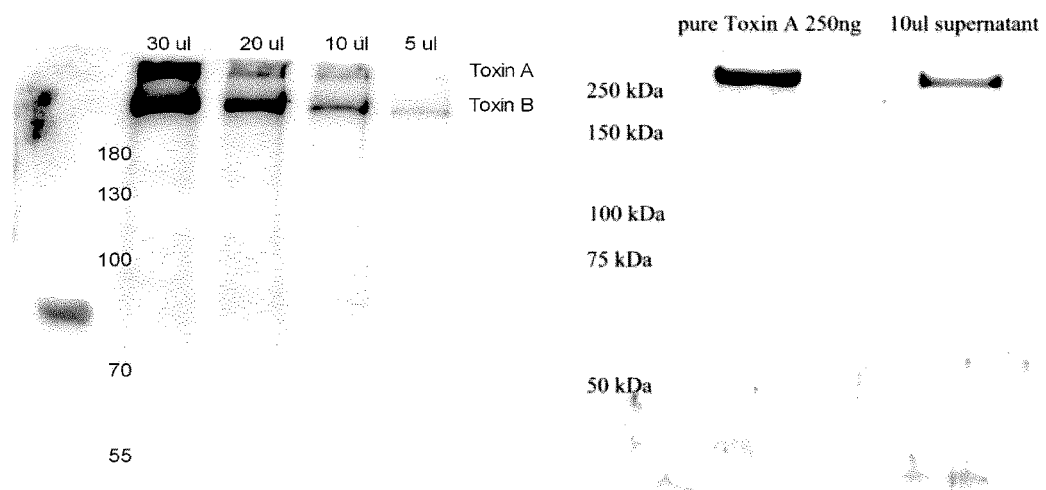
FIGURE 3                FIGURE 4
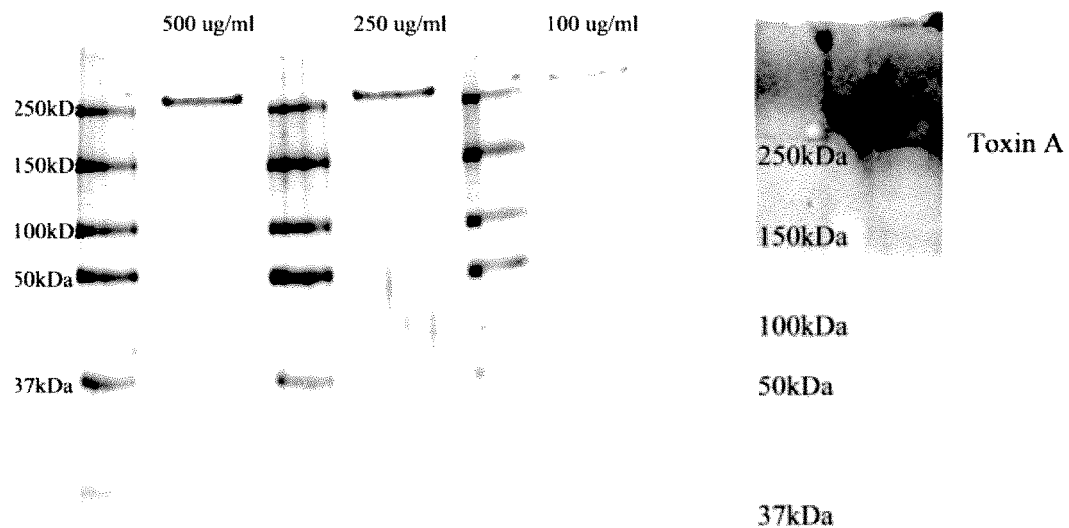
FIGURE 5                FIGURE 6

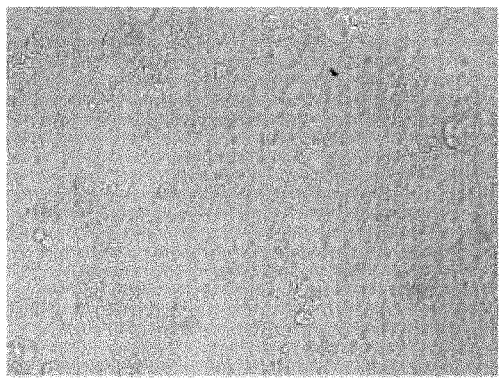
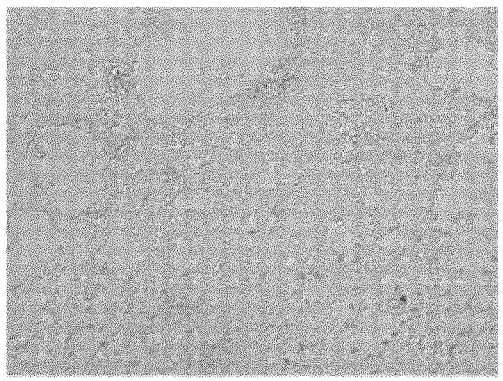
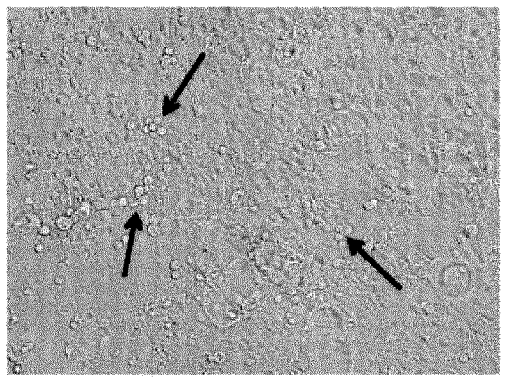
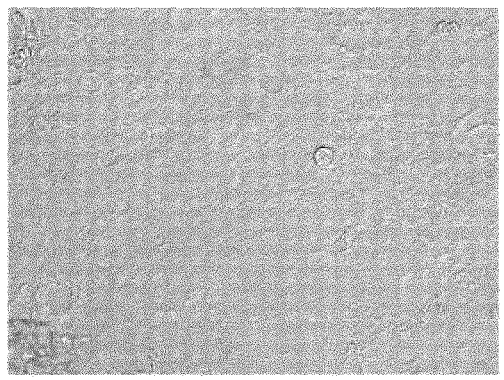
FIGURE 7

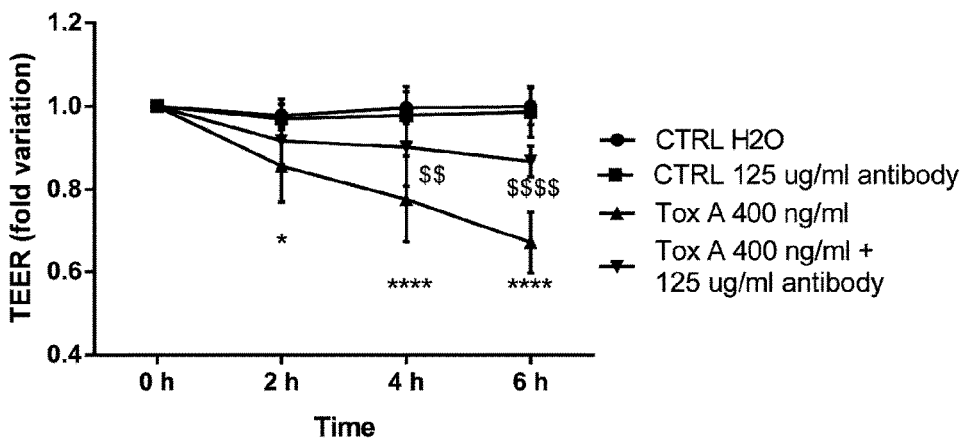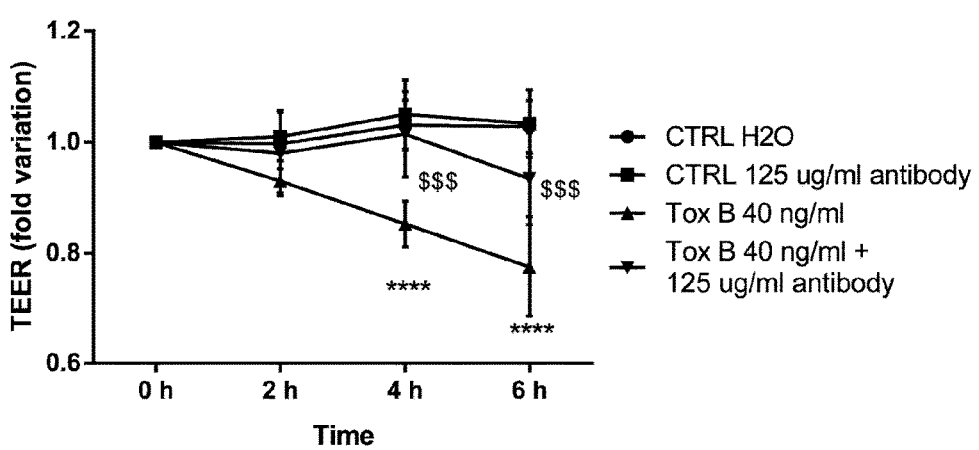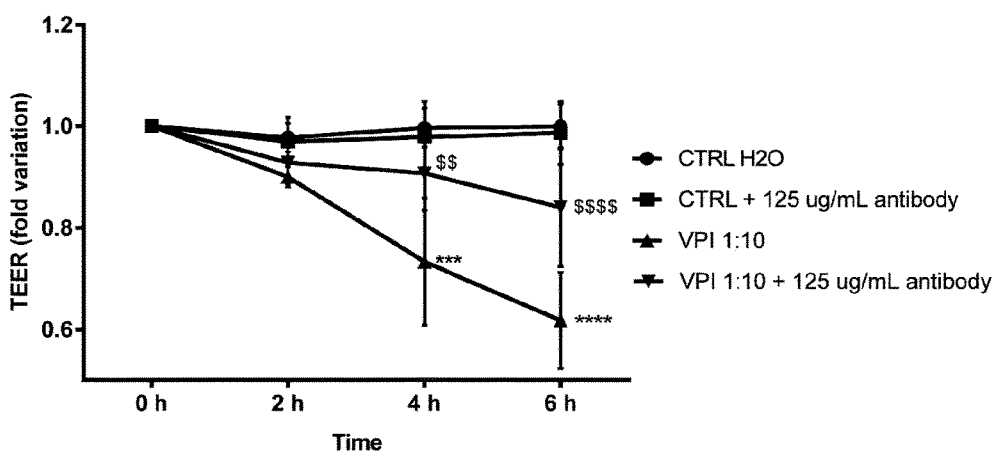
FIGURE 10

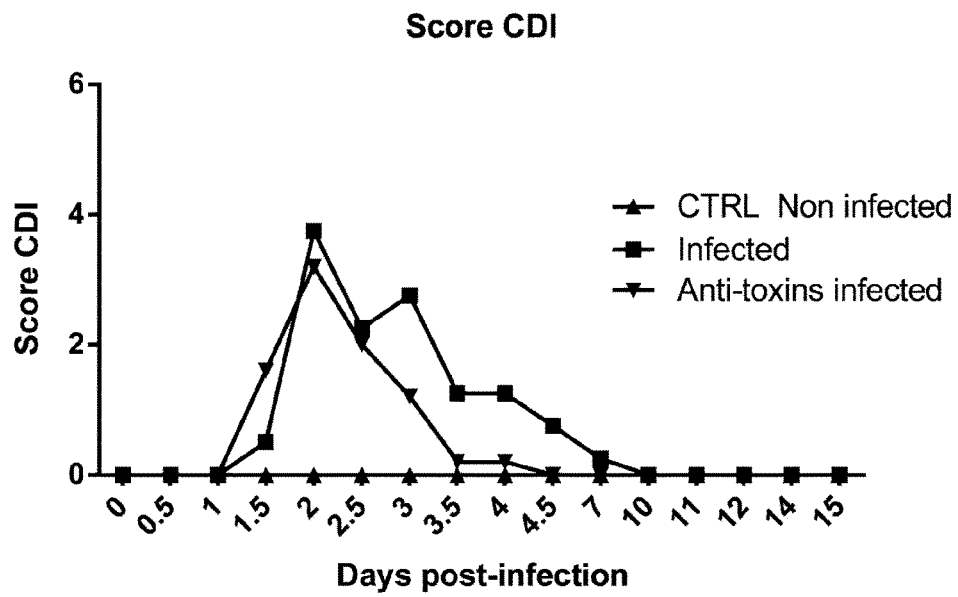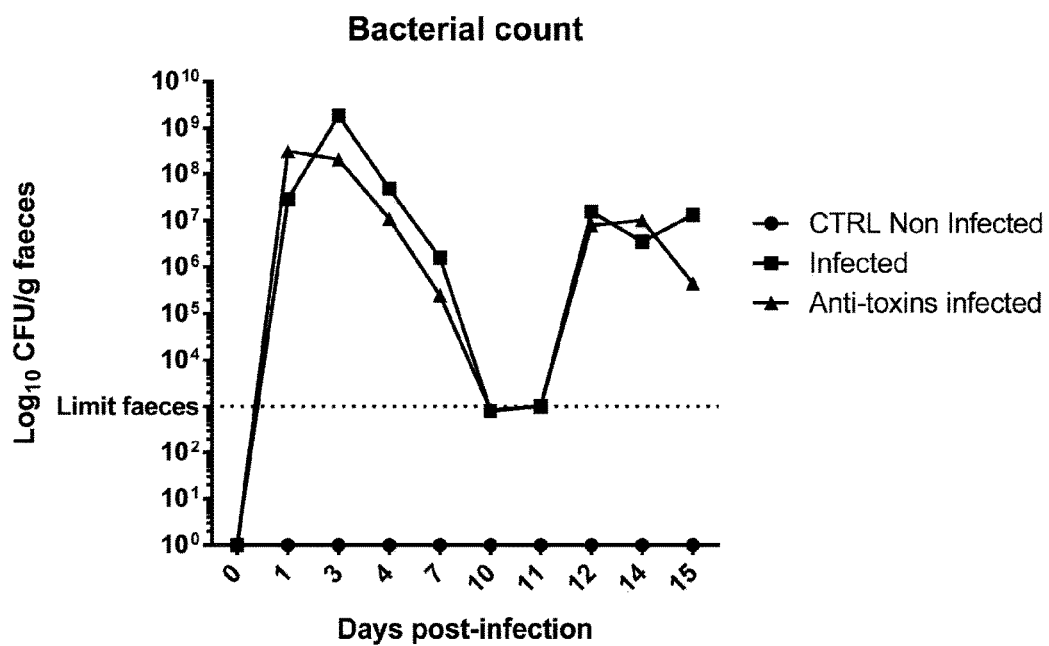
FIGURE 11

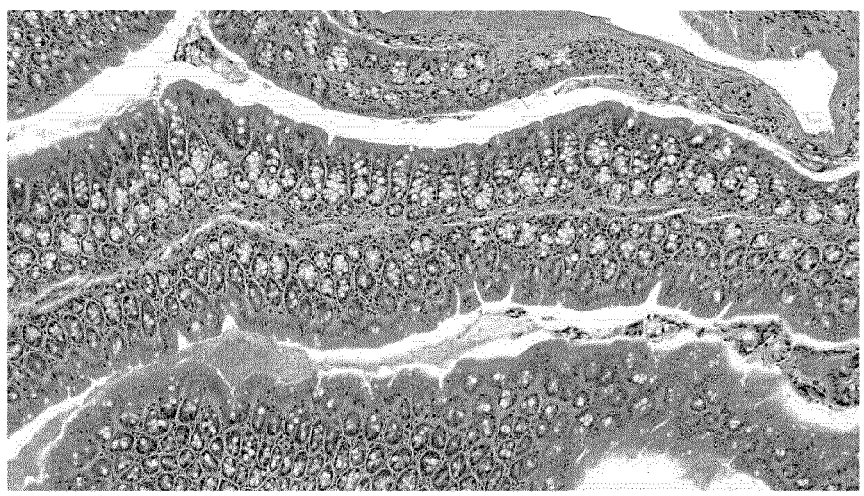
FIGURE 12

US 10,533,036 B2

CLOSTRIDIUM DIFFICILE TOXINS A AND/OR B ANTIGEN AND EPITOPE ANTIBODY, AND PHARMACEUTICAL USES THEREOF

CROSS-REFERENCE TO RELATED APPLICATIONS

The present patent application claims the benefits of priority of commonly assigned U.S. Patent Application No. 62/118,450, entitled "C difficile antibodies directed thereto, and target for the treatment of humans and other animals intoxicated with at least one bacterial toxin A and/or B." and filed at the United States Patent Trademark Office on Feb. 19, 2015; the content of which is incorporated herewith by reference.

FIELD OF THE INVENTION

The present invention generally relates to epitopes of toxins A and/or B produced by Clostridium difficile and antibodies that specifically binding to these epitopes. The invention is also related to pharmaceutical compositions and vaccines for the prevention or treatment of Clostridium difficile infection comprising any of the epitopes or antibodies thereof.

BACKGROUND OF THE INVENTION

Clostridium difficile is a Gram-positive, anaerobic, endospore-forming gastrointestinal pathogen responsible for C-difficile-associated disease (CDAD) in humans and animals with symptoms ranging in severity from mild cases of antibiotic-associated diarrhea to fatal pseudomembranous colitis (Rupnik et al, 2009; Leffler and Lamont, 2009; Songer, 2004; Kelly et al, 1994). Each year in North America, 1-3% of hospitalized patients receiving antibiotics become infected with C-difficile, leading to thousands of deaths and over $1 billion in associated costs to the healthcare system (Wilkins and Lyerly, 2003; Kyne et al, 2002; Kelly et al, 1994). C-difficile produces two primary virulence factors, toxin A (TcdA) and toxin B (TcdB), which are large (308 kDa and 269 kDa, respectively), single-subunit exotoxins composed of a catalytic, a translocation and a cell-receptor binding domain (RBD) (Jank and Aktories, 2008; Jank et al, 2007). Recently it was suggested TcdB is solely responsible for C-difficile virulence (Lyras et al, 2009), although earlier studies have shown both anti-TcdA and anti-TcdB monoclonal antibodies (mAbs) were required for full protection of hamsters from CDAD (Babcock et al, 2006; Kink and Williams, 1998) and anti-TcdA mAbs were required for protection in mice (Corthier et al, 1991).

The current approach for treating most CDAD infections involves administration of antibiotics, most commonly metronidazole or vancomycin (Leffler and Lamont, 2009). Antibiotic treatment places selection pressure on the organism, can lead to antibiotic resistance, and suppresses or eliminates beneficial commensal microbes. However, there are several other emerging challenges warranting the development of novel therapeutics. First, there is no acute CDAD treatment targeting TcdA and/or B. These toxins are responsible for loss of epithelial barrier function in the colon by disrupting tight junctions and increasing membrane permeability, causing diarrhea and promoting severe inflammation (Rupnik et al, 2009; Jank and Aktories, 2008). Second, hypervirulent strains of C-difficile, such as the NAP1/027 isolate, over-express TcdA and TcdB (Warny et al, 2005) and have been associated with increased mortality rates and disease severity (O'Connor et al, 2009; Pepin et al, 2005). Third, an estimated 20-25% of patients suffering from CDAD experience symptomatic relapse after the initial infection is cleared, with 45% of these patients prone to subsequent relapses (Johnson, 2009). Taken together, there is a need for non-antibiotic based reagents targeting and inhibiting TcdA and TcdB for CDAD therapy. Individuals who are asymptomatic C-difficile carriers and patients who experience mild cases of CDAD tend to possess high anti-toxin A titers (Kyne et al, 2001; Kyne et al, 2000; Warny et al, 1994; Viscidi et al, 1983). Conversely, patients susceptible to relapsing C-difficile infection have low anti-TcdA immunoglobulin titers, specifically IgM, IgG2 and IgG3 isotypes (Katchar et al, 2007; Kyne et al, 2001). TcdA-neutralizing secretory IgA antibodies are also thought to play a role in regulating CDAD severity (Johal et al 2004; Kelly et al 1992). Therefore, the introduction of anti-toxin antibodies to patients suffering from severe C-difficile infection may be a therapeutically useful approach.

A limited number of animal and human studies have illustrated the effectiveness of anti-toxin Abs for treatment of CDAD. Babcock et al (2006) intravenously administered anti-TcdA and anti-TcdB mAbs to hamsters and found a significant reduction in hamster mortality in prophylactic, primary disease and relapse models when both anti-toxin mAbs were administered. A recently completed clinical trial involving these two humanized mAbs appears promising (Lowy et al, 2010). In another study, intravenous administration of anti-TcdA mAbs raised against the RBD followed by oral challenge with C-difficile resulted in protection of mice (Corthier et al, 1991). Elsewhere, a toxoid vaccine given by the intraperitoneal route to hamsters conferred protection against oral C-difficile challenge (Giannasca et al, 1999) and mice vaccinated with DNA encoding the TcdA RBD resulted in full protection from oral TcdA challenge (Gardiner et al, 2009). In humans, a number of uncontrolled studies have reported intravenous immunoglobulin (IVIG) therapy to be successful for the treatment of severe CDAD (Juang et al, 2007; Hassoun and Ibrahim, 2007; McPherson et al, 2006; Wilcox, 2004; Salcedo et al, 1997; Leung et al, 1991). IVIG involves administration of high concentrations (150-400 mg/kg) of human immunoglobulins from healthy donors which are thought to contain neutralizing anti-toxin antibodies as an estimated 60% of healthy adults have detectable TcdA- and TcdB-specific serum IgG antibodies (Viscidi et al, 983). Given that C-difficile toxins rely on attachment to epithelial cells for entry (Jank and Aktories, 2008; Jank et al, 2007), neutralizing the toxins within the lower gastrointestinal tract with antibodies may block the first step in CDAD pathogenesis. In animals, orally administered bovine immunoglobulin concentrate (BIC) containing TcdA and TcdB neutralizing IgGs were able to prevent hamster mortality when used as a propholyactic (Lyerly et al, 1991) and protected rats from the enterotoxic effects of TcdA in vivo (Kelly et al, 1996). Chicken IgY antibodies specific for toxin RBDs were shown to reduce hamster mortality when administered orally to infected animals (Kink and Williams, 1998). In humans, there have been limited reports on CDAD therapy with orally delivered Abs. Tjellstrom et al (1993) reported the successful treatment of a 3½ year old boy suffering from severe CDAD with IgA antibody orally. Warny et al (1999) and Kelly et al (1997) examined the passage of anti-toxin bovine IgG through the human gastrointestinal tract and found a significant reduction in IgG activity, likely due to proteolytic degradation within the upper gastrointestinal tract. The limited success of both oral and systemic anti-toxin immunotherapy in clinical settings has likely been hampered by the high immunoglobulin dose requirements (150-400 mg/kg), the associated costs of these doses, and a lack of published clinical data showing the effectiveness of these treatments.

Despite such advances, there remains a need in the art for a safe and effective therapeutic for treating *C-difficile*-associated disease as well as for sensitive and effective reagents for the detection of toxins A and B, the factors responsible for *C-difficile*-associated disease.

SUMMARY OF THE INVENTION

The aforesaid and other objectives of the present invention are realized by generally providing specific *Clostridium difficile* (*C-difficile*) toxins A and/or B as a target for therapy, including passive immunotherapy, and particularly prevention of toxins A and/or B intoxication in human or other animals.

One aspect of the present invention is to provide an isolated polypeptide comprising a portion of *Clostridium difficile* toxins A and/or B sequence, the portion of toxins A and/or B sequence being an epitope for anti-toxins A and/or B antibody, the portion comprising a sequence being SEQ ID NO: 1, SEQ ID NO: 2, SEQ ID NO: 3, SEQ ID NO: 4, or any combination thereof.

Preferably, the portion of toxins A and/or B sequence may comprise a combination of SEQ ID NO: 1, SEQ ID NO: 2, SEQ ID NO: 3 and SEQ ID NO: 4.

The aforesaid isolated peptides may be used for immunizing an animal against *Clostridium difficile* infection.

Another aspect of the present invention is to provide a pharmaceutical composition for generating a neutralizing antibody directed against *Clostridium difficile* toxins A and/or B and comprising at least two different polypeptides, each polypeptide comprising a portion of *Clostridium difficile* toxins A and/or B sequence, the portion of toxins A and/or B sequence being an epitope for anti-toxins A and/or B antibody, and the portion comprising a sequence being SEQ ID NO: 1, SEQ ID NO: 2, SEQ ID NO: 3, SEQ ID NO: 4, or any combination thereof.

Preferably, the pharmaceutical composition may comprise four different polypeptides, wherein the portion of toxins A and/or B sequence comprises a combination of SEQ ID NO: 1, SEQ ID NO: 2, SEQ ID NO: 3 and SEQ ID NO: 4.

The aforesaid pharmaceutical compositions may further comprise a pharmaceutically acceptable carrier.

The pharmaceutical compositions may be used for immunizing an animal against *Clostridium difficile* infection.

Another aspect of the present invention is to provide a vaccine composition for prevention or treatment of *Clostridium difficile* infection comprising at least one polypeptide which comprises a portion of *Clostridium difficile* toxins A and/or B sequence,the portion of toxins A and/or B sequence being an epitope for anti-toxins A and/or B antibody, and the portion comprising a sequence being SEQ ID NO: 1, SEQ ID NO: 2, SEQ ID NO: 3, SEQ ID NO: 4, or any combination thereof.

Preferably, the aforesaid vaccine composition may comprise the portion of toxins A and/or B sequence comprising a combination of SEQ ID NO: 1, SEQ ID NO: 2, SEQ ID NO: 3 and SEQ ID NO: 4.

The aforesaid vaccine compositions may further comprise a pharmaceutically acceptable adjuvant.

Another aspect of the present invention is to provide a nucleic acid vaccine or DNA vaccine composition for prevention or treatment of *Clostridium difficile* infection comprising nucleic acids encoding at least one polypeptide which comprises a portion of *Clostridium difficile* toxins A and/or B sequence, the portion of toxins A and/or B sequence being an epitope for anti-toxins A and/or B antibody; the portion comprising a sequence being SEQ ID NO: 1, SEQ ID NO: 2, SEQ ID NO: 3, SEQ ID NO: 4, or any combination thereof.

Preferably, the aforesaid nucleic acid vaccine composition may comprise the portion of toxins A and/or B sequence comprising a combination of SEQ ID NO: 1, SEQ ID NO: 2, SEQ ID NO: 3 and SEQ ID NO: 4.

The aforesaid nucleic acid vaccine compositions may further comprise a pharmaceutically acceptable adjuvant.

Another aspect of the present invention is to provide a method of generating a neutralizing antibody directed against *Clostridium difficile* toxins A and/or B. The method comprises a first step of administrating to a host an isolated polypeptide comprising a portion of the *Clostridium difficile* toxins A and/or B sequence, the portion comprising a sequence being SEQ ID NO: 1, SEQ ID NO: 2, SEQ ID NO: 3, SEQ ID NO: 4, or any combination thereof, for generating antibodies in the host. The method also comprises a second step of obtaining the antibodies from the host. The host may be a mammal or a bird, including bird eggs, such as but not limited to chicken eggs.

Preferably, in the first step of the method, the portion of the *Clostridium difficile* toxins A and/or B sequence comprises a combination of SEQ ID NO: 1, SEQ ID NO: 2, SEQ ID NO: 3 and SEQ ID NO: 4.

Another aspect of the present invention is to provide a purified antibody adapted for binding to a toxins A and/or B peptide, the peptide comprising a sequence being SEQ ID NO: 1, SEQ ID NO: 2, SEQ ID NO: 3, SEQ ID NO: 4, or any combination thereof.

The aforesaid antibody may also be an active fragment thereof, a chimeric antibody, a veneered antibody, a humanized antibody or a single chain recombinant antibody based thereon as well as a bird polyclonal antibody or a bird humanized recombinant antibody.

The aforesaid antibody may be used for detecting pure toxins A and/or B or a presence of toxins A and/or B produced by *Clostridium difficile* in cell culture.

Another aspect of the present invention is to provide an antibody composition for prevention or treatment of *Clostridium difficile* infection, comprising different antibodies adapted for binding to at least two epitopes of toxins A and/or B, the at least two epitopes comprising a sequence being SEQ ID NO: 1, SEQ ID NO: 2, SEQ ID NO: 3, SEQ ID NO: 4, or any combination thereof.

Preferably, the aforesaid antibody composition may comprises different antibodies adapted for binding to four different epitopes, the epitopes comprising a combination of SEQ ID NO: 1, SEQ ID NO: 2, SEQ ID NO: 3 and SEQ ID NO: 4.

Another aspect of the present invention is to provide a pharmaceutical composition for the prevention or the treatment of *Clostridium difficile* toxins A and/or B intoxication, the composition comprising at least one antibody adapted for binding to at least one epitope of toxins A and/or B, the at least one epitope comprising a sequence being SEQ ID NO: 1, SEQ ID NO: 2, SEQ ID NO: 3, SEQ ID NO: 4, or any combination thereof.

Preferably, the aforesaid pharmaceutical composition may comprises at least one epitope comprising a combination of SEQ ID NO: 1, SEQ ID NO: 2, SEQ ID NO: 3 and SEQ ID NO: 4.

The aforesaid pharmaceutical compositions may further comprise a pharmaceutically acceptable carrier.

The aforesaid pharmaceutical compositions may be used for making a medicament for preventing or treating *Clostridium difficile* infection.

The aforesaid pharmaceutical compositions may also be used for the capture and neutralisation of *Clostridium difficile* toxins A and/or B, allowing a passive immunotherapy of mammals, such as humans.

The features of the present invention which are believed to be novel are set forth with particularity in the appended claims.

BRIEF DESCRIPTION OF THE DRAWINGS

The above and other objects, features and advantages of the invention will become more readily apparent from the following description, reference being made to the accompanying drawings in which:

FIGS. 2A and 2B illustrates the amino acid sequences of *Clostridium difficile* toxins A (SEQ ID NO:5) and B (SEQ ID NO:6), respectively, with the targeted sequence portion of toxins A and/or B epitope antibodies underlined.

FIG. 3 is a photograph of a western blot showing recognition of toxins A and/or B by toxins A and/or B epitope antibody IBSCD1, according to a preferred embodiment of the present invention.

FIG. 4 is a photograph of a western blot showing recognition of toxins A and/or B by toxins A and/or B epitope antibody IBSCD2, according to a preferred embodiment of the present invention.

FIG. 5 is a photograph of a western blot showing recognition of toxins A and/or B by toxins A and/or B epitope antibody IBSCD3, according to a preferred embodiment of the present invention.

FIG. 6 is a photograph of a western blot showing recognition of toxins A and/or B by toxins A and/or B epitope antibody IBSCD4, according to a preferred embodiment of the present invention.

FIG. 7 is a set of microscope photographs showing the neutralisation effect on the cell rounding and dead of Caco-2 intestinal cell line by toxins A and/or B epitope antibodies formulation in presence of the supernatant of *C-difficile* NAP1/027 hypervirulent strain, according to a preferred embodiment of the present invention.

FIG. 10 is a set of graphs showing the protection of the Caco-2 monolayer integrity by the blocking antibodies against *C-difficile* toxin A and/or B, according to a preferred embodiment of the present invention.

FIG. 11 is a set of graphs showing the reduction of *Clostridium difficile* infection in vivo by the blocking antibodies against *C-difficile* toxin A and/or B, according to a preferred embodiment of the present invention.

FIG. 12 is a set of microscope photographs showing the reduction of mucosal damage in murine colon by the blocking antibodies against *C-difficile* toxin A and/or B, according to a preferred embodiment of the present invention.

DETAILED DESCRIPTION OF THE PREFERRED EMBODIMENT

A novel composition of anti-toxins A and/or B antibodies and toxins A and/or B epitopes will be described hereinafter. Although the invention is described in terms of specific illustrative embodiment(s), it is to be understood that the embodiment(s) described herein are by way of example only and that the scope of the invention is not intended to be limited thereby.

Figure 1:
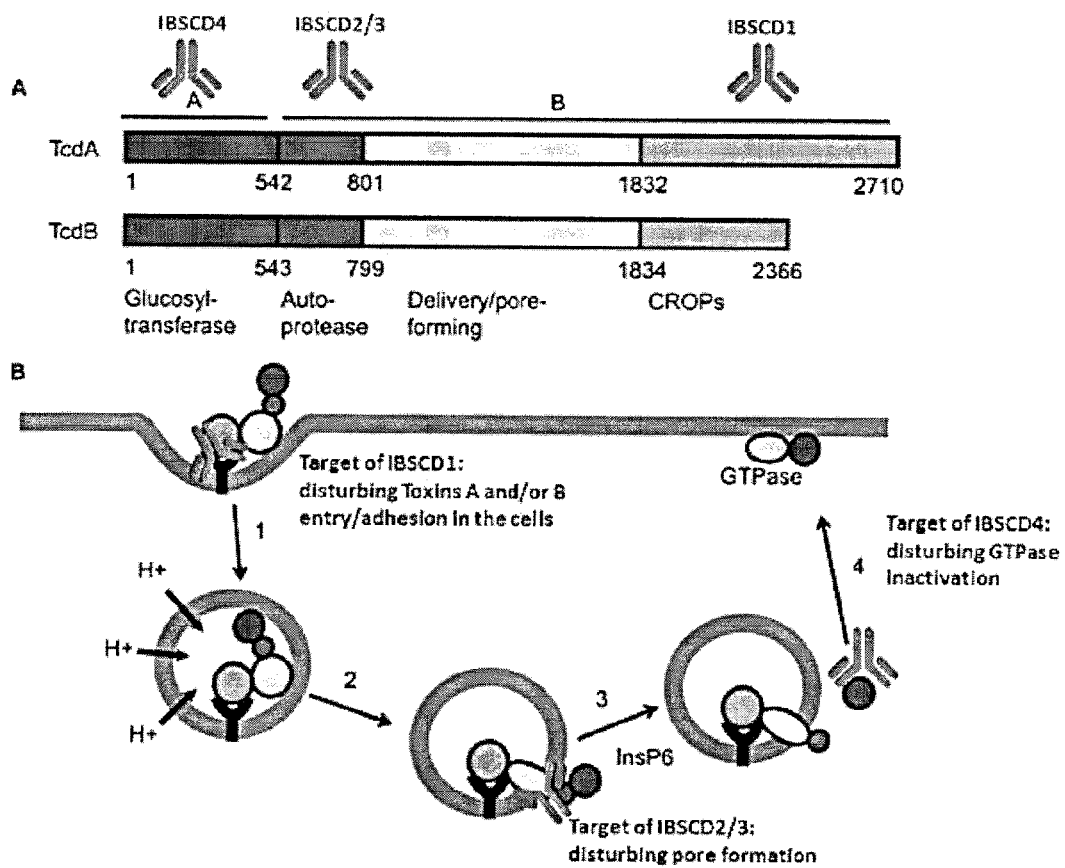
FIG. 1 is a schematic representation of the targeted portion of toxins A and/or B epitope antibodies.

A broad aspect, the present invention provides a method that uses a combination of toxins A and/or B epitope antibodies, including but not limited to bird's epitope antibodies, for the capture and neutralisation of *C-difficile* toxins A and/or B, which permit a passive immunotherapy of humans or others mammals. The method of neutralisation aims three different key portions of toxins A and/or B among the four domains of *C-difficile* toxins, which are the combined repetitive oligopeptides c-terminal domain (CROPs) 10, the delivery pore forming domain 20, the auto-protease domain 30, and the N-terminal glucosyltransferase domain 40, as illustrated in FIGS. 1 and 2. These different portions of toxins A and/or B includes four different epitopes adapted for generating toxins A and/or B epitope antibodies in mammals or birds. Furthermore, FIG. 2 shows the location of the four epitopes within the toxins A and B amino acid sequences as part of the present invention.

According to a first embodiment of the present invention, it is provided an isolated peptide having the amino acid sequence: DSKKYYFNTNTAEAA (SEQ ID NO: 1). This particular peptide is a toxins A and/or B epitope peptide encompassing amino acids 2084-2098 of toxins A and/or B, which has been identified as a shared toxins A and/or B epitope using the chicken polyclonal antibodies IBSCD1 (see FIG. 3).

According to a second embodiment of the present invention, it is provided an isolated peptide having the amino acid sequence: ANQYEVRINSEGR (SEQ ID NO: 2). This particular peptide is a toxins A and/or B epitope peptide encompassing amino acids 739-751 of toxins A and/or B, which has been identified as a shared toxins A and/or B epitope using the chicken polyclonal antibodies IBSCD2 (see FIG. 4).

According to a third embodiment of the present invention, it is provided an isolated peptide having the amino acid sequence GHGKDEFNTDIFAG (SEQ ID NO: 3). This particular peptide is a toxins A and/or B epitope peptide encompassing amino acids 652-665 of toxins A and/or B, which has been identified as a shared toxins A and/or B epitope using the chicken polyclonal antibodies IBSCD3 (see FIG. 5).

According to a forth embodiment of the present invention, it is provided an isolated peptide having the amino acid sequence DEYNKLTTNNNENKYL (SEQ ID NO: 4). This particular peptide is a toxins A and/or B epitope peptide encompassing amino acids 31-46 of toxins A and/or B, which has been identified as a shared toxins A and/or B epitope using the chicken polyclonal antibodies IBSCD4 (see FIG. 6).

In accordance with another embodiment of the present invention, the isolated peptides, including combinations of one or more thereof, are adapted for generating antibodies which recognize toxins A and/or B and have a neutralising therapeutic or prophylactic activity in immunizing animals, particularly mammals, most particularly humans, who have a *C-difficile* intoxication.

In accordance with a preferred embodiment of the present invention, it is provided a combination of polypeptides, which comprises all the afore-mentioned amino acid sequence of SEQ ID NO: 1, SEQ ID NO: 2, SEQ ID NO: 3 and SEQ ID NO: 4, or any combination thereof.

The afore-mentioned polypeptides may include an immunogenic peptide, particularly comprising amino acid sequence of any of SEQ ID NOS: 1-4, or an immunogenic fragment thereof. These polypeptides may also include immunogenic receptor of peptides, wherein such polypeptides comprise a combination of at least one immunogenic receptor peptide comprising amino acid sequence of any of SEQ ID NOS: 1-4, or immunogenic peptide fragment thereof.

In accordance with another embodiment of the present invention, it is provided a method for immunizing an animals, particularly mammals or birds comprising administering a toxins A and/or B epitope peptide or an immunogenic fragment thereof, whereby the animal produces antibodies that are immunoreactive with the epitope peptide exposed on partial or full length toxins A and/or B produced by *C-difficile* bacteria. The method for immunizing mammals or birds may comprise administering a toxins A and/or B peptide comprising amino acid sequence of any of SEQ ID NOS: 1-4 or an immunogenic fragment thereof, whereby the animal produces antibodies that are immunoreactive to full length toxins A and/or B produced by *C-difficile* bacteria. According to a preferred embodiment, the aforesaid method comprises the use of the four different toxins A and/or B peptides with the amino acid sequences of SEQ ID NO: 1, SEQ ID NO: 2, SEQ ID NO: 3 and SEQ ID NO: 4.

In accordance with another embodiment of the present invention, it is provided a pharmaceutical composition for generating a neutralizing antibody directed against *Clostridium difficile* toxins A and/or B, the pharmaceutical composition comprising a toxins A and/or B peptide, particularly with amino acid sequence of any of SEQ ID NOS: 1-4, and a pharmaceutically acceptable carrier. According to a preferred embodiment, the pharmaceutical composition comprises the four different toxins A and/or B peptides with the amino acid sequences of SEQ ID NO: 1, SEQ ID NO: 2, SEQ ID NO: 3 and SEQ ID NO: 4, and a pharmaceutically acceptable carrier.

In accordance with another embodiment of the present invention, it is provided a vaccines or immunogenic compositions that comprise one or more toxins A and/or B peptide, particularly with amino acid sequence of any of SEQ ID NOS: 1-4, and a pharmaceutically acceptable adjuvant. According to a preferred embodiment, the vaccine composition comprises the four different toxins A and/or B peptides with the amino acid sequences of SEQ ID NO: 1, SEQ ID NO: 2, SEQ ID NO: 3 and SEQ ID NO: 4, and a pharmaceutically acceptable adjuvant.

The vaccine may also be used for treatment of a subject, such as a mammal, particularly a human subject, suffering from a *C-difficile* intoxication. Such vaccine may comprise an immunogenic amount of one or more toxins A and/or B peptides, particularly with amino acid sequence of any of SEQ ID NOS: 1-4 or immunogenic fragment thereof, and a pharmaceutically acceptable adjuvant. The aforesaid toxins A and/or B peptides may be conjugated to a carrier.

In accordance with another embodiment of the present invention, it is provided a nucleic acid vaccines or DNA vaccines comprising nucleic acids encoding immunogenic toxins A and/or B peptides, particularly with amino acid sequence of any of SEQ ID NOS: 1-4, and a pharmaceutically acceptable adjuvant. According to a preferred embodiment, the nuclei acid vaccine composition comprises the nucleic acids encoding the four different toxins A and/or B peptides with the amino acid sequences of SEQ ID NO: 1, SEQ ID NO: 2, SEQ ID NO: 3 and SEQ ID NO: 4, and a pharmaceutically acceptable adjuvant. The aforementioned nucleic acid vaccine may further comprises at least one other polypeptide, particularly an immunomodulatory molecule peptide derived from *C-difficile*.

In accordance with another embodiment of the present invention, it is provided a method for diagnosis of *Clostridium difficile* infection comprising the steps of contacting a biological sample of a subject with at least one peptide fragment of toxins A and/or B and detecting antigen-antibody complex formation. Such at least one peptide fragment may comprises an epitope for anti-toxins A and/or B antibody with an amino acid sequence of any of SEQ ID NO: 1, SEQ ID NO: 2, SEQ ID NO: 3, SEQ ID NO: 4, or any combination thereof.

In accordance with another embodiment of the present invention, it is provided a kit for the diagnosis or detection of *Clostridium difficile* infection, the kit comprising at least one peptide fragment of toxins A and/or B and directions for diagnosing or detecting anti-toxin A and/or B antibody. Such at least one peptide fragment may comprise an epitope for anti-toxin A and/or B antibody with an amino acid sequence of any of SEQ ID NO: 1, SEQ ID NO: 2, SEQ ID NO: 3, SEQ ID NO: 4, or any combination thereof.

As previously mentioned, toxins A and/or B polypeptides with the amino acid sequence of any of SEQ ID NOS: 1-4 are adapted for generating toxins A and/or B epitope antibodies in mammals or birds. Such antibodies recognize toxins A and/or B and have neutralising effect on the activity of these toxins, so that the antibodies may be used for a therapeutic or prophylactic treatment against *C-difficile* intoxication in humans and animals.

In accordance with another embodiment of the present invention, it is provided a method of generating a neutralizing antibody directed against *Clostridium difficile* toxins A and/or B. The method comprises a first step of administrating to a host an isolated polypeptide comprising a portion of the *Clostridium difficile* toxins A and/or B sequence. The portion comprising a sequence being SEQ ID NO: 1, SEQ ID NO: 2, SEQ ID NO: 3, SEQ ID NO: 4, or any combination thereof, for generating antibodies in the host. The method comprises a second step of obtaining the antibodies from the host. The host may be a mammal or a bird, including the bird eggs, such as but not limited to chicken eggs.

The aforesaid method may also comprise a first step, wherein the portion of the *Clostridium difficile* toxins A and/or B sequence comprises a sequence being SEQ ID NO: 1, SEQ ID NO: 2, SEQ ID NO: 3 and SEQ ID NO: 4.

Referring to FIG. 3, an antibody, called IBSCD1, is adapted for binding to a key toxins A and/or B epitope, encompassing amino acids 2084-2098 of toxin A and/or B located in combined repetitive oligopeptides c-terminal domain (CROPs) 10 of toxins A and/or B. This domain plays a role in the binding to human or animal cells, as illustrated in FIG. 1, step 1.

Referring to FIGS. 4 and 5, two antibodies, called IBSCD2 and IBSCD3, are adapted for binding to toxins A and/or B epitopes, encompassing respectively amino acids 739-751 and 652-665 of toxins A and/or B located in the delivery pore forming domain 20. This domain plays a role in the endosome pore formation of the infected cell, as illustrated in FIG. 1, step 3.

Referring to FIG. 6, another antibody, called IBSCD4, bind the toxins A and/or B epitope encompassing amino acids 31-46 of toxins A and/or B located in the glucosyl-transferase domain 40. This domain plays a role in the inactivation of small GTPases in the affected cells, as illustrated in FIG. 1, step 4.

In accordance with a preferred embodiment of the present invention, it is provided a novel formulation that combines key toxins A and/or B epitope antibodies, located in three key domains of toxins A and/or B, for neutralisation of the toxins A and/or B, at any stage of toxins A and/or B intoxication related to *C-difficile* infection. Therefore, the novel formulation of toxins A and/or B epitope antibodies may be used in immunotherapy, for therapeutic and/or prophylactic mediation of *C-difficile* intoxication.

In accordance with another embodiment, it is provided a purified antibody to a toxin A and/or B peptide comprising the amino acid sequence of any of SEQ ID NOS: 1-4. The above-described antibodies may specifically detect pure toxins A and/or B or the presence of these toxins produced by *C-difficile* in culture.

The antibody may be selected from antibodies IBSCD1, IBSCD2, IBSCD3, IBSCD4 or active fragments thereof. The antibody may include both polyclonal and monoclonal antibodies prepared by known genetic techniques, as well as bi-specific antibodies, and antibodies including other functionalities suiting them for diagnostic or therapeutic use. The antibody may consist of bird polyclonal or bird humanized recombinant antibodies. Furthermore, the antibody may include, but not limited to, naturally raised and recombinant prepared antibodies or fragments thereof, including single chain variants and Fv. The antibodies may also include chimereic antibodies, veneered antibodies, humanized antibodies, chicken polyclonal antibodies, chicken recombinant humanized antibodies, domain antibodies, calemized antibodies and single chain recombinant antibodies. Such antibodies can be used for passive immunization to reduce *C-difficile* intoxication, particularly in humans.

In accordance with another embodiment of the present invention, it is provided a pharmaceutical composition for preventing or treating *C-difficile* toxins A and/or B intoxication. The pharmaceutical composition may comprise at least one antibody adapted for binding to at least one epitope of toxins A and/or B, and a pharmaceutically acceptable carrier. Such epitope may comprise a amino acid sequence of any of SEQ ID NO: 1, SEQ ID NO: 2, SEQ ID NO: 3, SEQ ID NO: 4, or any combination thereof. According to a preferred embodiment, the pharmaceutical composition comprises the antibodies adapted for binding to the four different toxins A and/or B peptides with the amino acid sequences of SEQ ID NO: 1, SEQ ID NO: 2, SEQ ID NO: 3 and SEQ ID NO: 4, and a pharmaceutically acceptable carrier.

In accordance with a another embodiment of the present invention, it is provided therapeutic methods based upon the activity of an antibody, or active fragments thereof, adapted for binding to a toxins A and/or B peptide comprising amino acid sequence of any of SEQ ID NOS: 1-4. In particular, the method may comprise antibodies, or active fragments thereof, and chimeric or synthetic antibodies derived therefrom, and can be prepared in pharmaceutical compositions, including a suitable vehicle, carrier or diluent, for administration in instances wherein therapy is appropriate, such as to treat *C-difficile* infection. Such methods may include oral formulations of avian of mammal anti-toxins A and/or B for prevention of toxins A and/or B intoxication. Such methods may also include modulating the half-life of the binding members, antibodies or fragments by methods known in the art such as pegylation. Such methods may further comprise additional antibodies or therapeutic agents.

In accordance with a another embodiment of the present invention, it is provided a method for diagnosis of *Clostridium difficile* infection comprising the steps of contacting a biological sample of a subject with at least one anti-toxins A and/or B antibody adapted for binding to at least one epitope of toxins A and/or B, and detecting antigen-antibody complex formation. Such at least one epitope may comprise an amino acid sequence of any of SEQ ID NO: 1, SEQ ID NO: 2, SEQ ID NO: 3, SEQ ID NO: 4, or any combination thereof.

In accordance with a another embodiment of the present invention, it is provided a kit for the diagnosis or detection of *Clostridium difficile* infection, the kit comprising at least one anti-toxins A and/or B antibody adapted for binding to at least one epitope of toxins A and/or B, and directions for diagnosing or detecting anti-toxin A and/or B antibody. Such at least one epitope may an amino acid sequence of any of SEQ ID NO: 1, SEQ ID NO: 2, SEQ ID NO: 3, SEQ ID NO: 4, or any combination thereof.

EXAMPLES

FIG. 7 shows the neutralisation effect on the cell rounding and dead of Caco-2 intestinal cell line by toxins A and/or B epitope antibodies formulation in presence of the supernatant of *C-difficile* NAP1/027 hypervirulent strain. Panel A) shows intact monolayer of Caco-2 cells after incubation with 25 µl of water (negative control). Panel B) shows disturbed and destroyed monolayer of Caco-2 cells, with a lot of cell rounding and dead cells after incubation with 25 µl of undiluted NAP1/027 strain *C-difficile* toxin A/B supernatant. Panel C) shows disturbed monolayer of Caco-2 cells, with cell rounding (arrows) and dead cells after incubation with 25 µl of 1:1000 dilution of NAP1/027 strain *C-difficile* toxin A/B supernatant. Panel D) shows preserved monolayer of Caco-2 cells after incubation with 25 µl of 1:1000 dilution of NAP1/027 strain *C-difficile* toxin A/B supernatant in the presence of a formulation containing 63 µg/ml of IBSCD1, IBSCD2, IBSCD3 and IBSCD4 toxins A/B epitope antibodies.

Figure 8:
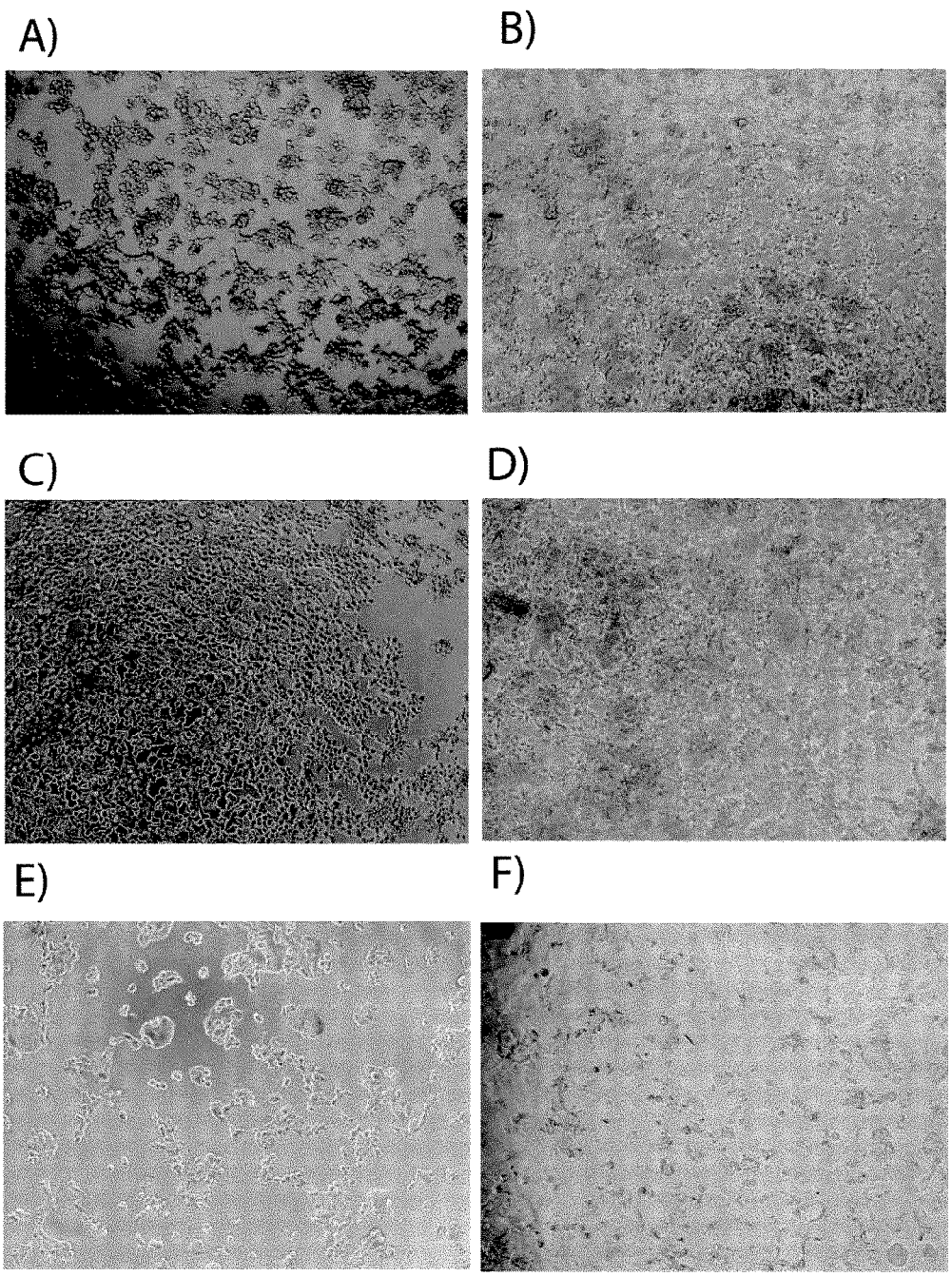
FIG. 8 is a set of microscope photographs showing the neutralisation effect on the cell rounding and dead of Caco-2 intestinal cell line by toxins A and/or B epitope antibodies formulation in presence of the supernatant of *C-difficile* NAP1/027 hypervirulent strain and purified toxin A and toxin B, according to a preferred embodiment of the present invention.

FIG. 8 shows the neutralisation effect on the cell rounding and dead of Caco-2 intestinal cell line by adding toxins A and/or B epitope antibodies formulation when in presence of the supernatant of *C-difficile* NAP1/027 hypervirulent strain and purified toxin A and toxin B. Panel A) shows complete rounding of cells, lost of adhesion and cells death after incubation with 400 ng/mL of purified toxin A. Panel B) shows reduction of cytotoxic effect, with decrease in rounding and cell death, after incubation with 400 ng/mL toxin A, preincubated with 63 µg/mL of IBSCD1, IBSCD2, IBSCD3 and IBSCD4 toxins A and/or B epitope antibodies. Panel C) shows disturbed monolayer of Caco-2 cells, with cell rounding and dead cells and without dome formation, after incubation with 25 µl of 1:100 dilution of NAP1/027 strain *C-difficile* toxin A/B supernatant. Panel D) shows preserved monolayer of Caco-2 cells after incubation with 25 µl of 1:100 dilution of NAP1/027 strain *C-difficile* toxin A and/or B supernatant in the presence of a formulation containing 125 µg/ml of IBSCD1, IBSCD2, IBSCD3 and IBSCD4 toxins A and/or B epitope antibodies. Panel E) shows complete rounding of cells, lost of adhesion and cell death after incubation with 10 ng/mL of purified toxin B. Panel F) shows reduction of cytotoxic effect, with decrease in rounding and cell death after incubation with 40 ng/mL toxin B, preincubated with 125 µg/mL of IBSCD1, IBSCD2, IBSCD3 and IBSCD4 toxins A and/or B epitope antibodies.

Figure 9:
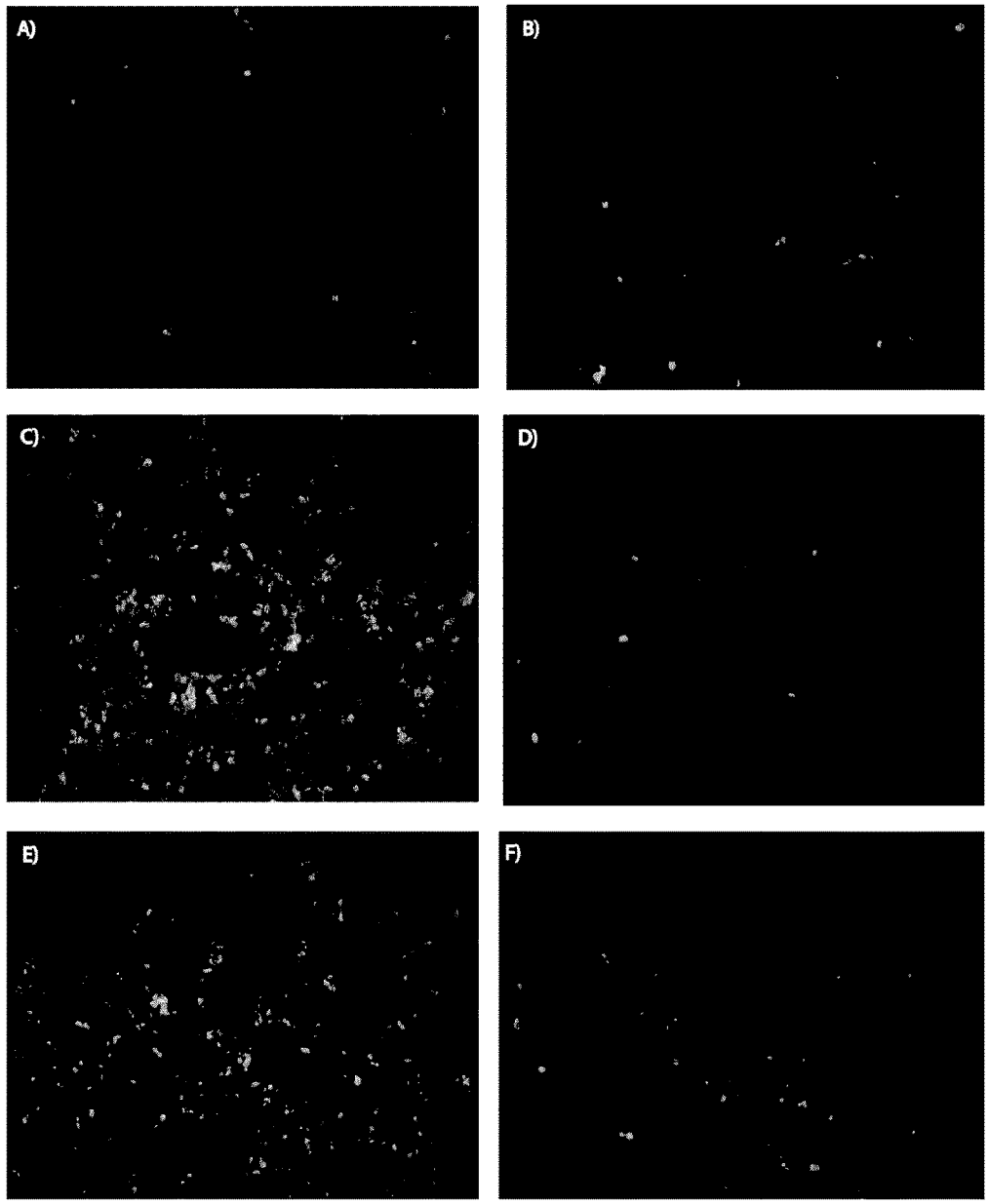
FIG. 9 is a set of epifluorescence microscope photographs showing improvement of Caco-2 cell viability by the blocking antibodies against *C-difficile* toxin A and/or B, according to a preferred embodiment of the present invention.

FIG. 9 shows cell death induced by *C. difficile* toxin A and B in Caco-2 cells and the improvement of cell viability by the blocking antibodies. Caco-2 cells were seeded in chamber slides in 200 µL of culture medium and incubated overnight at 37° C. in $CO_2$ incubator. The following day, cell death was induced with toxin A and B and cells were incubated for 48 h. Cells were washed with PBS and incubated with Annexin V and PI (1:10) for 15 min. Coverslips were mounted with mounting medium and DAPI. Images were taken by epifluorescence microscopy. Panel A) shows little or no cell death in cells treated with water. Panel B) shows little or no cell death due to a normal process of cell death in the presence of 125 µg/mL of IBSCD1, IBSCD2, IBSCD3 and IBSCD4 Toxins A and/or B epitope antibodies. Panel C) shows increased in number of green (or white), Annexin V labelled cells representing apoptotic cells, in the presence of 400 ng/mL toxin A. Panel D) shows a decrease in cell death with 400 ng/mL toxin A preincubated with 125 µg/mL of IBSCD1, IBSCD2, IBSCD3 and IBSCD4 toxins A and/or B epitope antibodies. Panel E) shows an increase in cell death with 40 ng/mL toxin B. Panel F) shows a decrease in cell death with 40 ng/mL toxin B preincubated with 125 µg/mL of IBSCD1, IBSCD2, IBSCD3 and IBSCD4 toxins A/B epitope antibodies. *C. difficile* toxins A and B induced programmed cell death and even necrosis (represented in white), while preincubation of toxins with IBSCD1, IBSCD2, IBSCD3 and IBSCD4 toxins A/B epitope antibodies deceased number of apoptotic cells in all conditions. Bleu, DAPI labelled cells represent live cells.

FIG. 10 shows the protection of the integrity of Caco-2 monolayer by the blocking antibodies against *C. difficile* toxin A and B. Panel A) shows 7-10 days post-confluent Caco-2 monolayer that was grown on porous 4 µm inserts. Only polarized monolayers of cell were used. At 6 h, the transepithelial electric resistance (TEER) of the Caco-2 monolayer rapidly decreased down to 67% when cells were stimulated with 400 ng/ml toxin A. Cells treated with toxin A preincubated with blocking antibodies IBSCD1, IBSCD2, IBSCD3 and IBSCD4 increased TEER up to 86% compared to unstimulated cells, which were reported to one. Panel B) shows the rapid decrease of the transepithelial electric resistance (TEER) of the Caco-2 monolayer down to 77% when cells were stimulated with 40 ng/ml toxin B compared to unstimulated cells. Use of 125 µg/ml of blocking antibodies restored epithelial integrity up to 93%. Panel C) shows that when cells were stimulates with supernatant of *C. difficile* NAP1/027 strain (1:10), TEER decreased to 61% compared to unstimulated after 6 h. Preincubation of 125 µg/ml IBSCD1, IBSCD2, IBSCD3 and IBSCD4 toxins A and/or B epitope antibodies with supernatant restored epithelial integrity up to 84%. Results represent the mean SEM of three independent experiments performed in duplicate. Statistical analysis was done with 2 way ANOVA.

FIG. 11 shows the reduction of *Clostridium difficile* infection in vivo by the blocking antibodies against *C-difficile* toxin A and/or B. 6-8 weeks old female mice were housed in groups of 4 in sterile cages equipped with HEPA filters and containing sterile bedding. They had access to sterile food and water ad libitum. Mice are intrinsically resistant to CDI, so they were be pre-conditioned for three days with 250 mg/L clindamycin and 400 mg/L streptomycin in the drinking water, followed by an intraperitoneal (i.p.) injection of 1 mg clindamycin/mouse to disrupt their intestinal microbiota and make them susceptible to CDI. Twenty-four hours later, mice received by gavage 10e+5 spores of the epidemic CD strain R20291 to initiate the infection. Mice were gaved twice a day with 1 mg of a preparation of IBSCD1, IBSCD2, IBSCD3 and IBSCD4 toxins A and/or B epitope antibodies in 0.1M carbonate buffer (pH 9.2) to neutralize the gastric acidity for 5 days. Control groups consist of uninfected mice, and infected but untreated mice. Panel A) shows the results from mice that were observed for a total of 7-10 days and clinical symptoms were monitored daily (diarrhea, weight loss, lethargy, etc.). Panel B) shows results from fresh fecal samples that were collected daily and homogenized in pre-reduced PBS, and CD were enumerated on agar plates. Clinical score end bacterial counts were the higher in untreated mice in comparison with uninfected mice. Mice receiving IBSCD1, IBSCD2, IBSCD3 and IBSCD4 toxins A and/or B epitope antibodies had lower CDI score then untreated mice and lower bacterial counts.

FIG. 12 shoes the reduction of mucosal damage in murine colon by the blocking antibodies against *C-difficile* toxin A and/or B. 6-8 weeks old female mice were housed in groups of 4 in sterile cages equipped with HEPA filters and containing sterile bedding. They had access to sterile food and water ad libitum. Mice are intrinsically resistant to CDI, so they were be pre-conditioned for three days with 250 mg/L clindamycin and 400 mg/L streptomycin in the drinking water, followed by an intraperitoneal (i.p.) injection of 1 mg clindamycin/mouse to disrupt their intestinal microbiota and make them susceptible to CDI. Twenty-four hours later, mice received by gavage 10e+5 spores of the epidemic CD strain R20291 to initiate the infection. Mice were gaved twice a day with 1mg of a preparation of IBSCD1, IBSCD2, IBSCD3 and IBSCD4 toxins A and/or B epitope antibodies in 0.1M carbonate buffer (pH 9.2) to neutralize the gastric acidity for 5 days. Control groups consist of uninfected mice, and infected but untreated mice. At day ten, colons were extracted and embedded in paraffin. Hematoxylin & Eosin (H&E) staining was performed. Panel A) shows normal H&E staining of uninfected mice. Panel B) shows H&E staining of infected but untreated mice, which presented signs of mild inflammation. Panel C) shows H&E staining of infected mice treated with IBSCD1, IBSCD2, IBSCD3 and IBSCD4 toxins A and/or B epitope antibodies, which presented less severe mucosal damage then untreated mice. Black arrows indicates thickness of submucosal layer, immune cell infiltration and lost of epithelial layer.

LIST OF REFERENCES

Babcock, G. J., T. J. Broering, et al. (2006). "Human monoclonal antibodies directed against toxins A and B prevent *Clostridium difficile*-induced mortality in hamsters." Infect Immun 74(11): 6339-47.

Corthier, G., M. C. Muller, et al. (1991). "Protection against experimental pseudomembranous colitis in gnotobiotic mice by use of monoclonal antibodies against *Clostridiumdifficile* toxin A." Infect Immun 59(3): 1192-5.

Gardiner, D. F., T. Rosenberg, et al. (2009). "A DNA vaccine targeting the receptor-binding domain of *Clostridium difficile* toxin A." Vaccine 27(27): 3598-604.

Giannasca, P. J., Z. X. Zhang, et al. (1999). "Serum antitoxin antibodies mediate systemic and mucosal protection from *Clostridium difficile* disease in hamsters." Infect Immun 67(2): 527-38.

Hassoun, A. and F. Ibrahim (2007). "Use of intravenous immunoglobulin for the treatment of severe *Clostridium difficile* colitis." Am J Geriatr Pharmacother 5(1): 48-51.

Jank, T. and K. Aktories (2008). "Structure and mode of action of clostridial glucosylating toxins: the ABCD model." Trends Microbiol 16(5): 222-9.

Jank, T., T. Giesemann, et al. (2007). "Rho-glucosylating *Clostridium difficile* toxins A and B: new insights into structure and function." Glycobiology 17(4): 15R-22R.

Johal, S. S., C. P. Lambert, et al. (2004). "Colonic IgA producing cells and macrophages are reduced in recurrent and non-recurrent *Clostridium difficile* associated diarrhoea." J Clin Pathol 57(9): 973-9.

Johnson, S. (2009). "Recurrent *Clostridium difficile* infection: a review of risk factors, treatments, and outcomes." J Infect 58(6): 403-10.

Juang, P., S. J. Skledar, et al. (2007). "Clinical outcomes of intravenous immune globulin in severe *clostridium difficile*-associated diarrhea." Am J Infect Control 35(2): 131-7.

Katchar, K., C. P. Taylor, et al. (2007). "Association between IgG2 and IgG3 subclass responses to toxin A and recurrent *Clostridium difficile*-associated disease." Clin Gastroenterol Hepatol 5(6): 707-13.

Kelly, C. P., C. Pothoulakis, et al. (1994). "*Clostridium difficile* colitis." N Engl J Med 330(4): 257-62.

Kelly, C. P., C. Pothoulakis, et al. (1992). "Human colonic aspirates containing immunoglobulin A antibody to *Clostridium difficile* toxin A inhibit toxin A-receptor binding." Gastroenterology 102(1): 35-40.

Kelly, C. P., C. Pothoulakis, et al. (1996). "Anti-*Clostridium difficile* bovine immunoglobulin concentrate inhibits cytotoxicity and enterotoxicity of *C. difficile* toxins." Antimicrob Agents Chemother 40(2): 373-9.

Kink, J. A. and J. A. Williams (1998). "Antibodies to recombinant *Clostridium difficile* toxins A and B are an effective treatment and prevent relapse of *C. difficile*-associated disease in a hamster model of infection." Infect Immun 66(5): 2018-25.

Kyne, L., M. B. Hamel, et al. (2002). "Health care costs and mortality associated with nosocomial diarrhea due to *Clostridium difficile*." Clin Infect Dis 34(3): 346-53.

Kyne, L., M. Warny, et al. (2000). "Asymptomatic carriage of *Clostridium difficile* and serum levels of IgG antibody against toxin A." N Engl J Med 342(6): 390-7.

Kyne, L., M. Warny, et al. (2001). "Association between antibody response to toxin A and protection against recurrent *Clostridium difficile* diarrhoea." Lancet 357 (9251): 189-93.

Leffler, D. A. and J. T. Lamont (2009). "Treatment of *Clostridium difficile*-associated disease." Gastroenterology 136(6): 1899-912.

Leung, D. Y., C. P. Kelly, et al. (1991). "Treatment with intravenously administered gamma globulin of chronic relapsing colitis induced by *Clostridium difficile* toxin." J Pediatr 118(4 Pt 1): 633-7.

Lowy, I., D. C. Molrine, et al. "Treatment with monoclonal antibodies against *Clostridium difficile* toxins." N Engl J Med 362(3): 197-205.

Lyerly, D. M., E. F. Bostwick, et al. (1991). "Passive immunization of hamsters against disease caused by *Clostridium difficile* by use of bovine immunoglobulin G concentrate." Infect Immun 59(6): 2215-8.

Lyras, D., J. R. O'Connor, et al. (2009). "Toxin B is essential for virulence of *Clostridium difficile*." Nature 458(7242): 1176-9.

McPherson, S., C. J. Rees, et al. (2006). "Intravenous immunoglobulin for the treatment of severe, refractory, and recurrent *Clostridium difficile* diarrhea." Dis Colon Rectum 49(5): 640-5.

O'Connor, J. R., S. Johnson, et al. (2009). "*Clostridium difficile* infection caused by the epidemic B1/NAP1/027 strain." Gastroenterology 136(6): 1913-24.

Pepin, J., N. Saheb, et al. (2005). "Emergence of fluoroquinolones as the predominant risk factor for *Clostridium difficile*-associated diarrhea: a cohort study during an epidemic in Quebec." Clin Infect Dis 41(9): 1254-60.

Rupnik, M., M. H. Wilcox, et al. (2009). "*Clostridium difficile* infection: new developments in epidemiology and pathogenesis." Nat Rev Microbiol 7(7): 526-36.

Salcedo, J., S. Keates, et al. (1997). "Intravenous immunoglobulin therapy for severe *Clostridium difficile* colitis." Gut 41(3): 366-70.

Songer, J. G. (2004). "The emergence of *Clostridium difficile* as a pathogen of food animals." Anim Health Res Rev 5(2): 321-6.

Tjellstrom, B., L. Stenhammar, et al. (1993). "Oral immunoglobulin A supplement in treatment of *Clostridium difficile* enteritis." Lancet 341(8846): 701-2.

Viscidi, R., B. E. Laughon, et al. (1983). "Serum antibody response to toxins A and B of *Clostridium difficile*." J Infect Dis 148(1): 93-100.

Warny, M., A. Fatimi, et al. (1999). "Bovine immunoglobulin concentrate-*clostridium difficile* retains *C difficile* toxin neutralising activity after passage through the human stomach and small intestine." Gut 44(2): 212-7.

Warny, M., J. Pepin, et al. (2005). "Toxin production by an emerging strain of *Clostridium difficile* associated with outbreaks of severe disease in North America and Europe." Lancet 366(9491): 1079-84.

Warny, M., J. P. Vaerman, et al. (1994). "Human antibody response to *Clostridium difficile* toxin A in relation to clinical course of infection." Infect Immun 62(2): 384-9.

Wilcox, M. H. (2004). "Descriptive study of intravenous immunoglobulin for the treatment of recurrent *Clostridium difficile* diarrhoea." J Antimicrob Chemother 53(5): 882-4.

Wilkins, T. D. and D. M. Lyerly (2003). "*Clostridium difficile* testing: after 20 years, still challenging." J Clin Microbiol 41(2): 531-4.

While illustrative and presently preferred embodiment(s) of the invention have been described in detail hereinabove, it is to be understood that the inventive concepts may be otherwise variously embodied and employed and that the appended claims are intended to be construed to include such variations except insofar as limited by the prior art.

What is claimed is:

1. An immunogenic composition comprising (i) a first peptide consisting of the sequence set forth in SEQ ID NO: 1, and (ii) a vaccine carrier conjugated to said first peptide.

2. The immunogenic composition of claim 1, wherein the composition further comprises (a) a second peptide comprising the sequence set forth in SEQ ID NO: 2; (b) a third peptide comprising the sequence set forth in SEQ ID NO: 3; (c) a fourth peptide comprising the sequence set forth in SEQ ID NO: 4; or (d) any combination of (a) to (c).

3. The immunogenic composition of claim 1, for use for immunizing an animal against *Clostridium difficile* infection.

4. The immunogenic composition of claim 1, further comprising
a pharmaceutically acceptable carrier.

5. The immunogenic composition of claim 2, wherein the composition further comprises (a) a second peptide comprising the sequence set forth in SEQ ID NO: 2; (b) a third peptide comprising the sequence set forth in SEQ ID NO: 3; and (c) a fourth peptide comprising the sequence set forth in SEQ ID NO: 4.

6. The immunogenic composition of claim 4, for use for immunizing an animal against *Clostridium difficile* infection.

7. The immunogenic composition of claim 1, further comprising
an effective amount of a pharmaceutically acceptable adjuvant.

8. The immunogenic composition of claim 2, further comprising an effective amount of a pharmaceutically acceptable adjuvant.

9. The immunogenic composition of claim 1, wherein the composition further comprises a second peptide consisting of the sequence set forth in SEQ ID NO: 2, wherein said second peptide is conjugated to a vaccine carrier.

10. The immunogenic composition of claim 1, wherein the composition further comprises a second peptide consisting of the sequence set forth in SEQ ID NO: 2; a third peptide consisting of the sequence set forth in SEQ ID NO: 3; and a fourth peptide consisting of the sequence set forth in SEQ ID NO: 4, wherein said second peptide, third peptide and fourth peptide are conjugated to a vaccine carrier.

11. The immunogenic vaccine composition of claim 7, wherein the composition further comprises a second peptide consisting of the sequence set forth in SEQ ID NO: 2, wherein said second peptide is conjugated to a vaccine carrier.

12. A method for generating neutralizing antibodies directed against *Clostridium difficile* toxins A and B in a host, the method comprising administering an effective amount of the immunogenic composition of claim 1 to the host.

13. A method for generating neutralizing antibodies directed against *Clostridium difficile* toxins A and B in a host, the method comprising administering an effective amount of the immunogenic composition of claim 9 to the host.

14. A method for generating neutralizing antibodies directed against *Clostridium difficile* toxins A and B in a host, the method comprising administering an effective amount of the immunogenic composition of claim 7 to the host.

15. A method for generating neutralizing antibodies directed against *Clostridium difficile* toxins A and B in a host, the method comprising administering an effective amount of the immunogenic composition of claim 11 to the host.

16. The method of claim 12, wherein the host is a mammal or a bird.

17. The method of claim 16, wherein the host is a bird.

* * * * *

SEQUENCE LISTING

<160> NUMBER OF SEQ ID NOS: 6

<210> SEQ ID NO 1

-continued

```
<211> LENGTH: 15
<212> TYPE: PRT
<213> ORGANISM: Clostridium difficile

<400> SEQUENCE: 1

Asp Ser Lys Lys Tyr Tyr Phe Asn Thr Asn Thr Ala Glu Ala Ala
1               5                   10                  15

<210> SEQ ID NO 2
<211> LENGTH: 13
<212> TYPE: PRT
<213> ORGANISM: Clostridium difficile

<400> SEQUENCE: 2

Ala Asn Gln Tyr Glu Val Arg Ile Asn Ser Glu Gly Arg
1               5                   10

<210> SEQ ID NO 3
<211> LENGTH: 14
<212> TYPE: PRT
<213> ORGANISM: Clostridium difficile

<400> SEQUENCE: 3

Gly His Gly Lys Asp Glu Phe Asn Thr Asp Ile Phe Ala Gly
1               5                   10

<210> SEQ ID NO 4
<211> LENGTH: 16
<212> TYPE: PRT
<213> ORGANISM: Clostridium difficile

<400> SEQUENCE: 4

Asp Glu Tyr Asn Lys Leu Thr Thr Asn Asn Glu Asn Lys Tyr Leu
1               5                   10                  15

<210> SEQ ID NO 5
<211> LENGTH: 2710
<212> TYPE: PRT
<213> ORGANISM: Clostridium difficile

<400> SEQUENCE: 5

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
                20                  25                  30

Tyr Asn Lys Leu Thr Thr Asn Asn Glu Asn Lys Tyr Leu Gln Leu
            35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                    85                  90                  95

Leu His Phe Val Trp Ile Gly Gly Glu Val Ser Asp Ile Ala Leu Glu
                100                 105                 110

Tyr Ile Lys Gln Trp Ala Asp Ile Asn Ala Glu Tyr Asn Ile Lys Leu
            115                 120                 125

Trp Tyr Asp Ser Glu Ala Phe Leu Val Asn Thr Leu Lys Lys Ala Ile
        130                 135                 140

Val Glu Ser Ser Thr Thr Glu Ala Leu Gln Leu Leu Glu Glu Glu Ile
145                 150                 155                 160
```

-continued

Gln Asn Pro Gln Phe Asp Asn Met Lys Phe Tyr Lys Arg Met Glu
            165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
            195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
            245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
            275                 280                 285

Leu Pro Gly Ile His Ser Asp Leu Phe Lys Thr Ile Ser Arg Pro Ser
            290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
            325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
            355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
            405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
            435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
            485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
            515                 520                 525

Gln Phe Glu Lys Tyr Val Arg Asp Tyr Thr Gly Gly Ser Leu Ser Glu
            530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
            565                 570                 575

```
Lys Asn Tyr Val His Tyr Ile Ile Gln Leu Gln Gly Asp Asp Ile Ser
                580             585                 590

Tyr Glu Ala Thr Cys Asn Leu Phe Ser Lys Asn Pro Lys Asn Ser Ile
            595                 600             605

Ile Ile Gln Arg Asn Met Asn Glu Ser Ala Lys Ser Tyr Phe Leu Ser
610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
                660                 665                 670

Leu Ser Asn Glu Ile Ser Ser Phe Leu Asp Thr Ile Lys Leu Asp Ile
                675                 680                 685

Ser Pro Lys Asn Val Glu Val Asn Leu Leu Gly Cys Asn Met Phe Ser
                690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
                740                 745                 750

Arg Lys Glu Leu Leu Ala His Ser Gly Lys Trp Ile Asn Lys Glu Glu
                755                 760                 765

Ala Ile Met Ser Asp Leu Ser Ser Lys Glu Tyr Ile Phe Phe Asp Ser
                770                 775                 780

Ile Asp Asn Lys Leu Lys Ala Lys Ser Lys Asn Ile Pro Gly Leu Ala
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
                820                 825                 830

Ser Ile Gly Asp Tyr Ile Tyr Tyr Glu Lys Leu Glu Pro Val Lys Asn
                835                 840                 845

Ile Ile His Asn Ser Ile Asp Asp Leu Ile Asp Glu Phe Asn Leu Leu
                850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
                900                 905                 910

Val Glu Thr Glu Lys Glu Ile Phe Ser Lys Tyr Ser Glu His Ile Thr
                915                 920                 925

Lys Glu Ile Ser Thr Ile Lys Asn Ser Ile Ile Thr Asp Val Asn Gly
                930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
                980                 985                 990

Ala Gln Leu Phe Ser Thr Gly Leu  Asn Thr Ile Tyr Asp  Ser Ile Gln
```

-continued

```
               995              1000              1005
Leu  Val  Asn  Leu  Ile  Ser  Asn  Ala  Val  Asn  Asp  Thr  Ile  Asn  Val
          1010              1015              1020

Leu  Pro  Thr  Ile  Thr  Glu  Gly  Ile  Pro  Ile  Val  Ser  Thr  Ile  Leu
          1025              1030              1035

Asp  Gly  Ile  Asn  Leu  Gly  Ala  Ala  Ile  Lys  Glu  Leu  Leu  Asp  Glu
          1040              1045              1050

His  Asp  Pro  Leu  Leu  Lys  Lys  Glu  Leu  Glu  Ala  Lys  Val  Gly  Val
          1055              1060              1065

Leu  Ala  Ile  Asn  Met  Ser  Leu  Ser  Ile  Ala  Ala  Thr  Val  Ala  Ser
          1070              1075              1080

Ile  Val  Gly  Ile  Gly  Ala  Glu  Val  Thr  Ile  Phe  Leu  Leu  Pro  Ile
          1085              1090              1095

Ala  Gly  Ile  Ser  Ala  Gly  Ile  Pro  Ser  Leu  Val  Asn  Asn  Glu  Leu
          1100              1105              1110

Ile  Leu  His  Asp  Lys  Ala  Thr  Ser  Val  Val  Asn  Tyr  Phe  Asn  His
          1115              1120              1125

Leu  Ser  Glu  Ser  Lys  Lys  Tyr  Gly  Pro  Leu  Lys  Thr  Glu  Asp  Asp
          1130              1135              1140

Lys  Ile  Leu  Val  Pro  Ile  Asp  Asp  Leu  Val  Ile  Ser  Glu  Ile  Asp
          1145              1150              1155

Phe  Asn  Asn  Asn  Ser  Ile  Lys  Leu  Gly  Thr  Cys  Asn  Ile  Leu  Ala
          1160              1165              1170

Met  Glu  Gly  Gly  Ser  Gly  His  Thr  Val  Thr  Gly  Asn  Ile  Asp  His
          1175              1180              1185

Phe  Phe  Ser  Ser  Pro  Ser  Ile  Ser  Ser  His  Ile  Pro  Ser  Leu  Ser
          1190              1195              1200

Ile  Tyr  Ser  Ala  Ile  Gly  Ile  Glu  Thr  Glu  Asn  Leu  Asp  Phe  Ser
          1205              1210              1215

Lys  Lys  Ile  Met  Met  Leu  Pro  Asn  Ala  Pro  Ser  Arg  Val  Phe  Trp
          1220              1225              1230

Trp  Glu  Thr  Gly  Ala  Val  Pro  Gly  Leu  Arg  Ser  Leu  Glu  Asn  Asp
          1235              1240              1245

Gly  Thr  Arg  Leu  Leu  Asp  Ser  Ile  Arg  Asp  Leu  Tyr  Pro  Gly  Lys
          1250              1255              1260

Phe  Tyr  Trp  Arg  Phe  Tyr  Ala  Phe  Phe  Asp  Tyr  Ala  Ile  Thr  Thr
          1265              1270              1275

Leu  Lys  Pro  Val  Tyr  Glu  Asp  Thr  Asn  Ile  Lys  Ile  Lys  Leu  Asp
          1280              1285              1290

Lys  Asp  Thr  Arg  Asn  Phe  Ile  Met  Pro  Thr  Ile  Thr  Thr  Asn  Glu
          1295              1300              1305

Ile  Arg  Asn  Lys  Leu  Ser  Tyr  Ser  Phe  Asp  Gly  Ala  Gly  Gly  Thr
          1310              1315              1320

Tyr  Ser  Leu  Leu  Leu  Ser  Ser  Tyr  Pro  Ile  Ser  Thr  Asn  Ile  Asn
          1325              1330              1335

Leu  Ser  Lys  Asp  Asp  Leu  Trp  Ile  Phe  Asn  Ile  Asp  Asn  Glu  Val
          1340              1345              1350

Arg  Glu  Ile  Ser  Ile  Glu  Asn  Gly  Thr  Ile  Lys  Lys  Gly  Lys  Leu
          1355              1360              1365

Ile  Lys  Asp  Val  Leu  Ser  Lys  Ile  Asp  Ile  Asn  Lys  Asn  Lys  Leu
          1370              1375              1380

Ile  Ile  Gly  Asn  Gln  Thr  Ile  Asp  Phe  Ser  Gly  Asp  Ile  Asp  Asn
          1385              1390              1395
```

```
Lys Asp Arg Tyr Ile Phe Leu Thr Cys Glu Leu Asp Asp Lys Ile
1400                1405               1410

Ser Leu Ile Ile Glu Ile Asn Leu Val Ala Lys Ser Tyr Ser Leu
1415                1420               1425

Leu Leu Ser Gly Asp Lys Asn Tyr Leu Ile Ser Asn Leu Ser Asn
1430                1435               1440

Thr Ile Glu Lys Ile Asn Thr Leu Gly Leu Asp Ser Lys Asn Ile
1445                1450               1455

Ala Tyr Asn Tyr Thr Asp Glu Ser Asn Asn Lys Tyr Phe Gly Ala
1460                1465               1470

Ile Ser Lys Thr Ser Gln Lys Ser Ile Ile His Tyr Lys Lys Asp
1475                1480               1485

Ser Lys Asn Ile Leu Glu Phe Tyr Asn Asp Ser Thr Leu Glu Phe
1490                1495               1500

Asn Ser Lys Asp Phe Ile Ala Glu Asp Ile Asn Val Phe Met Lys
1505                1510               1515

Asp Asp Ile Asn Thr Ile Thr Gly Lys Tyr Tyr Val Asp Asn Asn
1520                1525               1530

Thr Asp Lys Ser Ile Asp Phe Ser Ile Ser Leu Val Ser Lys Asn
1535                1540               1545

Gln Val Lys Val Asn Gly Leu Tyr Leu Asn Glu Ser Val Tyr Ser
1550                1555               1560

Ser Tyr Leu Asp Phe Val Lys Asn Ser Asp Gly His His Asn Thr
1565                1570               1575

Ser Asn Phe Met Asn Leu Phe Leu Asp Asn Ile Ser Phe Trp Lys
1580                1585               1590

Leu Phe Gly Phe Glu Asn Ile Asn Phe Val Ile Asp Lys Tyr Phe
1595                1600               1605

Thr Leu Val Gly Lys Thr Asn Leu Gly Tyr Val Glu Phe Ile Cys
1610                1615               1620

Asp Asn Asn Lys Asn Ile Asp Ile Tyr Phe Gly Glu Trp Lys Thr
1625                1630               1635

Ser Ser Ser Lys Ser Thr Ile Phe Ser Gly Asn Gly Arg Asn Val
1640                1645               1650

Val Val Glu Pro Ile Tyr Asn Pro Asp Thr Gly Glu Asp Ile Ser
1655                1660               1665

Thr Ser Leu Asp Phe Ser Tyr Glu Pro Leu Tyr Gly Ile Asp Arg
1670                1675               1680

Tyr Ile Asn Lys Val Leu Ile Ala Pro Asp Leu Tyr Thr Ser Leu
1685                1690               1695

Ile Asn Ile Asn Thr Asn Tyr Tyr Ser Asn Glu Tyr Tyr Pro Glu
1700                1705               1710

Ile Ile Val Leu Asn Pro Asn Thr Phe His Lys Lys Val Asn Ile
1715                1720               1725

Asn Leu Asp Ser Ser Ser Phe Glu Tyr Lys Trp Ser Thr Glu Gly
1730                1735               1740

Ser Asp Phe Ile Leu Val Arg Tyr Leu Glu Glu Ser Asn Lys Lys
1745                1750               1755

Ile Leu Gln Lys Ile Arg Ile Lys Gly Ile Leu Ser Asn Thr Gln
1760                1765               1770

Ser Phe Asn Lys Met Ser Ile Asp Phe Lys Asp Ile Lys Lys Leu
1775                1780               1785
```

-continued

```
Ser Leu Gly Tyr Ile Met Ser Asn Phe Lys Ser Phe Asn Ser Glu
1790                1795                1800

Asn Glu Leu Asp Arg Asp His Leu Gly Phe Lys Ile Ile Asp Asn
1805                1810                1815

Lys Thr Tyr Tyr Tyr Asp Glu Asp Ser Lys Leu Val Lys Gly Leu
1820                1825                1830

Ile Asn Ile Asn Asn Ser Leu Phe Tyr Phe Asp Pro Ile Glu Phe
1835                1840                1845

Asn Leu Val Thr Gly Trp Gln Thr Ile Asn Gly Lys Lys Tyr Tyr
1850                1855                1860

Phe Asp Ile Asn Thr Gly Ala Ala Leu Thr Ser Tyr Lys Ile Ile
1865                1870                1875

Asn Gly Lys His Phe Tyr Phe Asn Asn Asp Gly Val Met Gln Leu
1880                1885                1890

Gly Val Phe Lys Gly Pro Asp Gly Phe Glu Tyr Phe Ala Pro Ala
1895                1900                1905

Asn Thr Gln Asn Asn Asn Ile Glu Gly Gln Ala Ile Val Tyr Gln
1910                1915                1920

Ser Lys Phe Leu Thr Leu Asn Gly Lys Lys Tyr Tyr Phe Asp Asn
1925                1930                1935

Asn Ser Lys Ala Val Thr Gly Trp Arg Ile Ile Asn Asn Glu Lys
1940                1945                1950

Tyr Tyr Phe Asn Pro Asn Asn Ala Ile Ala Ala Val Gly Leu Gln
1955                1960                1965

Val Ile Asp Asn Asn Lys Tyr Tyr Phe Asn Pro Asp Thr Ala Ile
1970                1975                1980

Ile Ser Lys Gly Trp Gln Thr Val Asn Gly Ser Arg Tyr Tyr Phe
1985                1990                1995

Asp Thr Asp Thr Ala Ile Ala Phe Asn Gly Tyr Lys Thr Ile Asp
2000                2005                2010

Gly Lys His Phe Tyr Phe Asp Ser Asp Cys Val Val Lys Ile Gly
2015                2020                2025

Val Phe Ser Thr Ser Asn Gly Phe Glu Tyr Phe Ala Pro Ala Asn
2030                2035                2040

Thr Tyr Asn Asn Asn Ile Glu Gly Gln Ala Ile Val Tyr Gln Ser
2045                2050                2055

Lys Phe Leu Thr Leu Asn Gly Lys Lys Tyr Tyr Phe Asp Asn Asn
2060                2065                2070

Ser Lys Ala Val Thr Gly Leu Gln Thr Ile Asp Ser Lys Lys Tyr
2075                2080                2085

Tyr Phe Asn Thr Asn Thr Ala Glu Ala Ala Thr Gly Trp Gln Thr
2090                2095                2100

Ile Asp Gly Lys Lys Tyr Tyr Phe Asn Thr Asn Thr Ala Glu Ala
2105                2110                2115

Ala Thr Gly Trp Gln Thr Ile Asp Gly Lys Lys Tyr Tyr Phe Asn
2120                2125                2130

Thr Asn Thr Ala Ile Ala Ser Thr Gly Tyr Thr Ile Ile Asn Gly
2135                2140                2145

Lys His Phe Tyr Phe Asn Thr Asp Gly Ile Met Gln Ile Gly Val
2150                2155                2160

Phe Lys Gly Pro Asn Gly Phe Glu Tyr Phe Ala Pro Ala Asn Thr
2165                2170                2175

Asp Ala Asn Asn Ile Glu Gly Gln Ala Ile Leu Tyr Gln Asn Glu
```

-continued

```
            2180                2185                2190
Phe Leu Thr Leu Asn Gly Lys Lys Tyr Tyr Phe Gly Ser Asp Ser
    2195                2200                2205
Lys Ala Val Thr Gly Trp Arg Ile Ile Asn Asn Lys Lys Tyr Tyr
    2210                2215                2220
Phe Asn Pro Asn Asn Ala Ile Ala Ala Ile His Leu Cys Thr Ile
    2225                2230                2235
Asn Asn Asp Lys Tyr Tyr Phe Ser Tyr Asp Gly Ile Leu Gln Asn
    2240                2245                2250
Gly Tyr Ile Thr Ile Glu Arg Asn Asn Phe Tyr Phe Asp Ala Asn
    2255                2260                2265
Asn Glu Ser Lys Met Val Thr Gly Val Phe Lys Gly Pro Asn Gly
    2270                2275                2280
Phe Glu Tyr Phe Ala Pro Ala Asn Thr His Asn Asn Asn Ile Glu
    2285                2290                2295
Gly Gln Ala Ile Val Tyr Gln Asn Lys Phe Leu Thr Leu Asn Gly
    2300                2305                2310
Lys Lys Tyr Tyr Phe Asp Asn Asp Ser Lys Ala Val Thr Gly Trp
    2315                2320                2325
Gln Thr Ile Asp Gly Lys Lys Tyr Tyr Phe Asn Leu Asn Thr Ala
    2330                2335                2340
Glu Ala Ala Thr Gly Trp Gln Thr Ile Asp Gly Lys Lys Tyr Tyr
    2345                2350                2355
Phe Asn Leu Asn Thr Ala Glu Ala Ala Thr Gly Trp Gln Thr Ile
    2360                2365                2370
Asp Gly Lys Lys Tyr Tyr Phe Asn Thr Asn Thr Phe Ile Ala Ser
    2375                2380                2385
Thr Gly Tyr Thr Ser Ile Asn Gly Lys His Phe Tyr Phe Asn Thr
    2390                2395                2400
Asp Gly Ile Met Gln Ile Gly Val Phe Lys Gly Pro Asn Gly Phe
    2405                2410                2415
Glu Tyr Phe Ala Pro Ala Asn Thr Asp Ala Asn Asn Ile Glu Gly
    2420                2425                2430
Gln Ala Ile Leu Tyr Gln Asn Lys Phe Leu Thr Leu Asn Gly Lys
    2435                2440                2445
Lys Tyr Tyr Phe Gly Ser Asp Ser Lys Ala Val Thr Gly Leu Arg
    2450                2455                2460
Thr Ile Asp Gly Lys Lys Tyr Tyr Phe Asn Thr Asn Thr Ala Val
    2465                2470                2475
Ala Val Thr Gly Trp Gln Thr Ile Asn Gly Lys Lys Tyr Tyr Phe
    2480                2485                2490
Asn Thr Asn Thr Ser Ile Ala Ser Thr Gly Tyr Thr Ile Ile Ser
    2495                2500                2505
Gly Lys His Phe Tyr Phe Asn Thr Asp Gly Ile Met Gln Ile Gly
    2510                2515                2520
Val Phe Lys Gly Pro Asp Gly Phe Glu Tyr Phe Ala Pro Ala Asn
    2525                2530                2535
Thr Asp Ala Asn Asn Ile Glu Gly Gln Ala Ile Arg Tyr Gln Asn
    2540                2545                2550
Arg Phe Leu Tyr Leu His Asp Asn Ile Tyr Tyr Phe Gly Asn Asn
    2555                2560                2565
Ser Lys Ala Ala Thr Gly Trp Val Thr Ile Asp Gly Asn Arg Tyr
    2570                2575                2580
```

```
Tyr Phe Glu Pro Asn Thr Ala Met Gly Ala Asn Gly Tyr Lys Thr
    2585                2590                2595

Ile Asp Asn Lys Asn Phe Tyr Phe Arg Asn Gly Leu Pro Gln Ile
    2600                2605                2610

Gly Val Phe Lys Gly Ser Asn Gly Phe Glu Tyr Phe Ala Pro Ala
    2615                2620                2625

Asn Thr Asp Ala Asn Asn Ile Glu Gly Gln Ala Ile Arg Tyr Gln
    2630                2635                2640

Asn Arg Phe Leu His Leu Leu Gly Lys Ile Tyr Tyr Phe Gly Asn
    2645                2650                2655

Asn Ser Lys Ala Val Thr Gly Trp Gln Thr Ile Asn Gly Lys Val
    2660                2665                2670

Tyr Tyr Phe Met Pro Asp Thr Ala Met Ala Ala Ala Gly Gly Leu
    2675                2680                2685

Phe Glu Ile Asp Gly Val Ile Tyr Phe Phe Gly Val Asp Gly Val
    2690                2695                2700

Lys Ala Pro Gly Ile Tyr Gly
    2705                2710

<210> SEQ ID NO 6
<211> LENGTH: 2366
<212> TYPE: PRT
<213> ORGANISM: Clostridium difficile

<400> SEQUENCE: 6

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
                100                 105                 110

Asn Tyr Ile Asn Gln Trp Lys Asp Val Asn Ser Asp Tyr Asn Val Asn
            115                 120                 125

Val Phe Tyr Asp Ser Asn Ala Phe Leu Ile Asn Thr Leu Lys Lys Thr
        130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
                180                 185                 190

Gln Arg Glu Glu Asn Pro Glu Leu Ile Ile Asp Asp Ile Val Lys Thr
            195                 200                 205

Tyr Leu Ser Asn Glu Tyr Ser Lys Glu Ile Asp Glu Leu Asn Thr Tyr
        210                 215                 220

Ile Glu Glu Ser Leu Asn Lys Ile Thr Gln Asn Ser Gly Asn Asp Val
```

-continued

```
            225                 230                 235                 240
Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ser Asp Ile Leu
        260                 265                 270

Arg Ile Ser Ala Leu Lys Glu Ile Gly Met Tyr Leu Asp Val Asp
            275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
                340                 345                 350

Lys Ser Asp Lys Ser Glu Ile Phe Ser Ser Leu Gly Asp Met Glu Ala
            355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655
```

-continued

```
Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Ser Ile
        755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
        835                 840                 845

Ser Asp Ser Ile Asn Tyr Ile Lys Asp Glu Phe Lys Leu Ile Glu Ser
    850                 855                 860

Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
    930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr  Ile Thr Asp Ala Ala  Lys Val Val
        995                 1000                 1005

Glu Leu  Val Ser Thr Ala Leu  Asp Glu Thr Ile Asp  Leu Leu Pro
    1010                1015                 1020

Thr Leu  Ser Glu Gly Leu Pro  Ile Ile Ala Thr Ile  Ile Asp Gly
    1025                1030                 1035

Val Ser  Leu Gly Ala Ala Ile  Lys Glu Leu Ser Glu  Thr Ser Asp
    1040                1045                 1050

Pro Leu  Leu Arg Gln Glu Ile  Glu Ala Lys Ile Gly  Ile Met Ala
    1055                1060                 1065
```

```
Val Asn Leu Thr Thr Ala Thr Thr Ala Ile Ile Thr Ser Ser Leu
    1070            1075            1080

Gly Ile Ala Ser Gly Phe Ser Ile Leu Leu Val Pro Leu Ala Gly
    1085            1090            1095

Ile Ser Ala Gly Ile Pro Ser Leu Val Asn Asn Glu Leu Val Leu
    1100            1105            1110

Arg Asp Lys Ala Thr Lys Val Val Asp Tyr Phe Lys His Val Ser
    1115            1120            1125

Leu Val Glu Thr Glu Gly Val Phe Thr Leu Leu Asp Asp Lys Ile
    1130            1135            1140

Met Met Pro Gln Asp Asp Leu Val Ile Ser Glu Ile Asp Phe Asn
    1145            1150            1155

Asn Asn Ser Ile Val Leu Gly Lys Cys Glu Ile Trp Arg Met Glu
    1160            1165            1170

Gly Gly Ser Gly His Thr Val Thr Asp Asp Ile Asp His Phe Phe
    1175            1180            1185

Ser Ala Pro Ser Ile Thr Tyr Arg Glu Pro His Leu Ser Ile Tyr
    1190            1195            1200

Asp Val Leu Glu Val Gln Lys Glu Glu Leu Asp Leu Ser Lys Asp
    1205            1210            1215

Leu Met Val Leu Pro Asn Ala Pro Asn Arg Val Phe Ala Trp Glu
    1220            1225            1230

Thr Gly Trp Thr Pro Gly Leu Arg Ser Leu Glu Asn Asp Gly Thr
    1235            1240            1245

Lys Leu Leu Asp Arg Ile Arg Asp Asn Tyr Glu Gly Glu Phe Tyr
    1250            1255            1260

Trp Arg Tyr Phe Ala Phe Ile Ala Asp Ala Leu Ile Thr Thr Leu
    1265            1270            1275

Lys Pro Arg Tyr Glu Asp Thr Asn Ile Arg Ile Asn Leu Asp Ser
    1280            1285            1290

Asn Thr Arg Ser Phe Ile Val Pro Ile Ile Thr Thr Glu Tyr Ile
    1295            1300            1305

Arg Glu Lys Leu Ser Tyr Ser Phe Tyr Gly Ser Gly Gly Thr Tyr
    1310            1315            1320

Ala Leu Ser Leu Ser Gln Tyr Asn Met Gly Ile Asn Ile Glu Leu
    1325            1330            1335

Ser Glu Ser Asp Val Trp Ile Ile Asp Val Asp Asn Val Val Arg
    1340            1345            1350

Asp Val Thr Ile Glu Ser Asp Lys Ile Lys Lys Gly Asp Leu Ile
    1355            1360            1365

Glu Gly Ile Leu Ser Thr Leu Ser Ile Glu Glu Asn Lys Ile Ile
    1370            1375            1380

Leu Asn Ser His Glu Ile Asn Phe Ser Gly Glu Val Asn Gly Ser
    1385            1390            1395

Asn Gly Phe Val Ser Leu Thr Phe Ser Ile Leu Glu Gly Ile Asn
    1400            1405            1410

Ala Ile Ile Glu Val Asp Leu Leu Ser Lys Ser Tyr Lys Leu Leu
    1415            1420            1425

Ile Ser Gly Glu Leu Lys Ile Leu Met Leu Asn Ser Asn His Ile
    1430            1435            1440

Gln Gln Lys Ile Asp Tyr Ile Gly Phe Asn Ser Glu Leu Gln Lys
    1445            1450            1455

Asn Ile Pro Tyr Ser Phe Val Asp Ser Glu Gly Lys Glu Asn Gly
```

```
                    1460                1465                1470
Phe Ile Asn Gly Ser Thr Lys Glu Gly Leu Phe Val Ser Glu Leu
    1475                1480                1485
Pro Asp Val Val Leu Ile Ser Lys Val Tyr Met Asp Asp Ser Lys
    1490                1495                1500
Pro Ser Phe Gly Tyr Tyr Ser Asn Asn Leu Lys Asp Val Lys Val
    1505                1510                1515
Ile Thr Lys Asp Asn Val Asn Ile Leu Thr Gly Tyr Tyr Leu Lys
    1520                1525                1530
Asp Asp Ile Lys Ile Ser Leu Ser Leu Thr Leu Gln Asp Glu Lys
    1535                1540                1545
Thr Ile Lys Leu Asn Ser Val His Leu Asp Glu Ser Gly Val Ala
    1550                1555                1560
Glu Ile Leu Lys Phe Met Asn Arg Lys Gly Asn Thr Asn Thr Ser
    1565                1570                1575
Asp Ser Leu Met Ser Phe Leu Glu Ser Met Asn Ile Lys Ser Ile
    1580                1585                1590
Phe Val Asn Phe Leu Gln Ser Asn Ile Lys Phe Ile Leu Asp Ala
    1595                1600                1605
Asn Phe Ile Ile Ser Gly Thr Thr Ser Ile Gly Gln Phe Glu Phe
    1610                1615                1620
Ile Cys Asp Glu Asn Asp Asn Ile Gln Pro Tyr Phe Ile Lys Phe
    1625                1630                1635
Asn Thr Leu Glu Thr Asn Tyr Thr Leu Tyr Val Gly Asn Arg Gln
    1640                1645                1650
Asn Met Ile Val Glu Pro Asn Tyr Asp Leu Asp Asp Ser Gly Asp
    1655                1660                1665
Ile Ser Ser Thr Val Ile Asn Phe Ser Gln Lys Tyr Leu Tyr Gly
    1670                1675                1680
Ile Asp Ser Cys Val Asn Lys Val Val Ile Ser Pro Asn Ile Tyr
    1685                1690                1695
Thr Asp Glu Ile Asn Ile Thr Pro Val Tyr Glu Thr Asn Asn Thr
    1700                1705                1710
Tyr Pro Glu Val Ile Val Leu Asp Ala Asn Tyr Ile Asn Glu Lys
    1715                1720                1725
Ile Asn Val Asn Ile Asn Asp Leu Ser Ile Arg Tyr Val Trp Ser
    1730                1735                1740
Asn Asp Gly Asn Asp Phe Ile Leu Met Ser Thr Ser Glu Glu Asn
    1745                1750                1755
Lys Val Ser Gln Val Lys Ile Arg Phe Val Asn Val Phe Lys Asp
    1760                1765                1770
Lys Thr Leu Ala Asn Lys Leu Ser Phe Asn Phe Ser Asp Lys Gln
    1775                1780                1785
Asp Val Pro Val Ser Glu Ile Ile Leu Ser Phe Thr Pro Ser Tyr
    1790                1795                1800
Tyr Glu Asp Gly Leu Ile Gly Tyr Asp Leu Gly Leu Val Ser Leu
    1805                1810                1815
Tyr Asn Glu Lys Phe Tyr Ile Asn Asn Phe Gly Met Met Val Ser
    1820                1825                1830
Gly Leu Ile Tyr Ile Asn Asp Ser Leu Tyr Tyr Phe Lys Pro Pro
    1835                1840                1845
Val Asn Asn Leu Ile Thr Gly Phe Val Thr Val Gly Asp Asp Lys
    1850                1855                1860
```

```
Tyr Tyr Phe Asn Pro Ile Asn Gly Gly Ala Ala Ser Ile Gly Glu
1865                 1870                1875

Thr Ile Ile Asp Asp Lys Asn Tyr Tyr Phe Asn Gln Ser Gly Val
1880                 1885                1890

Leu Gln Thr Gly Val Phe Ser Thr Glu Asp Gly Phe Lys Tyr Phe
1895                 1900                1905

Ala Pro Ala Asn Thr Leu Asp Glu Asn Leu Glu Gly Glu Ala Ile
1910                 1915                1920

Asp Phe Thr Gly Lys Leu Ile Ile Asp Glu Asn Ile Tyr Tyr Phe
1925                 1930                1935

Asp Asp Asn Tyr Arg Gly Ala Val Glu Trp Lys Glu Leu Asp Gly
1940                 1945                1950

Glu Met His Tyr Phe Ser Pro Glu Thr Gly Lys Ala Phe Lys Gly
1955                 1960                1965

Leu Asn Gln Ile Gly Asp Tyr Lys Tyr Tyr Phe Asn Ser Asp Gly
1970                 1975                1980

Val Met Gln Lys Gly Phe Val Ser Ile Asn Asp Asn Lys His Tyr
1985                 1990                1995

Phe Asp Asp Ser Gly Val Met Lys Val Gly Tyr Thr Glu Ile Asp
2000                 2005                2010

Gly Lys His Phe Tyr Phe Ala Glu Asn Gly Glu Met Gln Ile Gly
2015                 2020                2025

Val Phe Asn Thr Glu Asp Gly Phe Lys Tyr Phe Ala His His Asn
2030                 2035                2040

Glu Asp Leu Gly Asn Glu Glu Gly Glu Glu Ile Ser Tyr Ser Gly
2045                 2050                2055

Ile Leu Asn Phe Asn Asn Lys Ile Tyr Tyr Phe Asp Asp Ser Phe
2060                 2065                2070

Thr Ala Val Val Gly Trp Lys Asp Leu Glu Asp Gly Ser Lys Tyr
2075                 2080                2085

Tyr Phe Asp Glu Asp Thr Ala Glu Ala Tyr Ile Gly Leu Ser Leu
2090                 2095                2100

Ile Asn Asp Gly Gln Tyr Tyr Phe Asn Asp Asp Gly Ile Met Gln
2105                 2110                2115

Val Gly Phe Val Thr Ile Asn Asp Lys Val Phe Tyr Phe Ser Asp
2120                 2125                2130

Ser Gly Ile Ile Glu Ser Gly Val Gln Asn Ile Asp Asp Asn Tyr
2135                 2140                2145

Phe Tyr Ile Asp Asp Asn Gly Ile Val Gln Ile Gly Val Phe Asp
2150                 2155                2160

Thr Ser Asp Gly Tyr Lys Tyr Phe Ala Pro Ala Asn Thr Val Asn
2165                 2170                2175

Asp Asn Ile Tyr Gly Gln Ala Val Glu Tyr Ser Gly Leu Val Arg
2180                 2185                2190

Val Gly Glu Asp Val Tyr Tyr Phe Gly Glu Thr Tyr Thr Ile Glu
2195                 2200                2205

Thr Gly Trp Ile Tyr Asp Met Glu Asn Glu Ser Asp Lys Tyr Tyr
2210                 2215                2220

Phe Asn Pro Glu Thr Lys Lys Ala Cys Lys Gly Ile Asn Leu Ile
2225                 2230                2235

Asp Asp Ile Lys Tyr Tyr Phe Asp Glu Lys Gly Ile Met Arg Thr
2240                 2245                2250
```

-continued

```
Gly Leu Ile Ser Phe Glu Asn Asn Tyr Tyr Phe Asn Glu Asn
    2255            2260                2265

Gly Glu Met Gln Phe Gly Tyr Ile Asn Ile Glu Asp Lys Met Phe
    2270                2275                2280

Tyr Phe Gly Glu Asp Gly Val Met Gln Ile Gly Val Phe Asn Thr
    2285                2290                2295

Pro Asp Gly Phe Lys Tyr Phe Ala His Gln Asn Thr Leu Asp Glu
    2300                2305                2310

Asn Phe Glu Gly Glu Ser Ile Asn Tyr Thr Gly Trp Leu Asp Leu
    2315                2320                2325

Asp Glu Lys Arg Tyr Tyr Phe Thr Asp Glu Tyr Ile Ala Ala Thr
    2330                2335                2340

Gly Ser Val Ile Ile Asp Gly Glu Glu Tyr Tyr Phe Asp Pro Asp
    2345                2350                2355

Thr Ala Gln Leu Val Ile Ser Glu
    2360                2365
```